US010271970B2

(12) United States Patent
Paul et al.

(10) Patent No.: US 10,271,970 B2
(45) Date of Patent: Apr. 30, 2019

(54) BLOOD PERFUSION DEVICE

(71) Applicant: Cook Medical Technologies LLC, Bloomington, IN (US)

(72) Inventors: Ram H. Paul, Bloomington, IN (US); Richard A. Swift, South Bend, IN (US); Oliver Bach, Neuenburg (DE); Ralf Steiner, Pforzheim (DE); Angela R. Barnett, Lafayette, IN (US); Keith R. Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/761,391

(22) Filed: Feb. 7, 2013

(65) Prior Publication Data

US 2013/0138202 A1    May 30, 2013

Related U.S. Application Data

(63) Continuation-in-part of application No. 13/197,511, filed on Aug. 3, 2011, now Pat. No. 9,192,463.
(Continued)

(51) Int. Cl.
*A61F 2/82*    (2013.01)
*A61F 2/915*   (2013.01)
(Continued)

(52) U.S. Cl.
CPC ............... *A61F 2/82* (2013.01); *A61F 2/07* (2013.01); *A61F 2/848* (2013.01); *A61F 2/915* (2013.01);
(Continued)

(58) Field of Classification Search
CPC .............. A61F 2/07; A61F 2002/075; A61F 2002/8483; A61F 2002/8486; A61F 2/915; A61F 2002/91558; A61F 2002/072
(Continued)

(56) References Cited

U.S. PATENT DOCUMENTS 5,397,355 A * 3/1995 Marin et al. .................. 623/1.2
5,591,226 A    1/1997 Trerotola et al.
(Continued)

FOREIGN PATENT DOCUMENTS

EP    0 732 088 A2    9/1996
GB    2 164 562 A     3/1986
(Continued)

OTHER PUBLICATIONS

U.S. Appl. No. 13/197,074, filed Aug. 3, 2011, Paul, Jr. et al.
PCT International Search Report and Written Opinion for PCT Application No. PCT/US2011/046446, dated Oct. 26, 2011.

*Primary Examiner* — Leslie Lopez
(74) *Attorney, Agent, or Firm* — Brinks Gilson & Lione

(57) ABSTRACT

A perfusion device and a delivery system for repair of a damaged portion of a body vessel. Perfusion device can include a tubular body that is self-expandable, having a proximal portion, a distal portion, and an intermediate portion. One or more series of barbs can be disposed circumferentially along the intermediate portion. Barbs are capable of penetrating into the tunica intima and tunica media of said vessel wall upon insertion of said device into said body vessel, and not into said tunica adventitia. A graft can be associated with the tubular body. Graft has a proximal end and a distal end, and preferably extends entirely along a luminal wall of the tubular body. Graft may also extend along an exterior surface of the tubular body at the proximal and distal portions. Delivery devices for the perfusion implant and methods of delivering the perfusion implant are also provided.

22 Claims, 11 Drawing Sheets

Related U.S. Application Data

(60) Provisional application No. 61/370,304, filed on Aug. 3, 2010.

(51) Int. Cl.
*A61F 2/07* (2013.01)
*A61F 2/848* (2013.01)

(52) U.S. Cl.
CPC . *A61F 2002/075* (2013.01); *A61F 2002/8483* (2013.01); *A61F 2002/91558* (2013.01); *A61F 2002/91575* (2013.01); *A61F 2210/0076* (2013.01); *A61F 2220/0016* (2013.01); *A61F 2220/0075* (2013.01); *A61F 2250/0023* (2013.01); *A61F 2250/0036* (2013.01); *A61F 2250/0037* (2013.01)

(58) Field of Classification Search
USPC .............................. 623/1.36, 1.14, 1.16, 1.13
See application file for complete search history.

(56) References Cited

U.S. PATENT DOCUMENTS

| | | | |
|---|---|---|---|
| 5,693,085 A * | 12/1997 | Buirge et al. | 623/1.13 |
| 5,800,526 A * | 9/1998 | Anderson | A61F 2/07 606/191 |
| 5,824,053 A | 10/1998 | Khosravi et al. | |
| 6,042,605 A * | 3/2000 | Martin et al. | 623/1.13 |
| 6,110,198 A | 8/2000 | Fogarty et al. | |
| 6,197,013 B1 | 3/2001 | Reed et al. | |
| 6,261,320 B1 | 7/2001 | Tam et al. | |
| 6,287,335 B1 | 9/2001 | Drasler et al. | |
| 6,729,356 B1 | 5/2004 | Baker et al. | |
| 7,044,962 B2 | 5/2006 | Elliott | |
| 7,500,986 B2 | 3/2009 | Lye et al. | |
| 7,670,366 B2 | 3/2010 | Case et al. | |
| 2001/0034550 A1 * | 10/2001 | Buirge | A61F 2/0022 623/1.47 |
| 2003/0065379 A1 | 4/2003 | Babbs et al. | |
| 2003/0074055 A1 | 4/2003 | Haverkost | |
| 2003/0120331 A1 | 6/2003 | Chobotov et al. | |
| 2003/0158595 A1 | 8/2003 | Randall et al. | |
| 2003/0176911 A1 * | 9/2003 | Iancea | A61F 2/07 623/1.13 |
| 2003/0236570 A1 * | 12/2003 | Cook et al. | 623/1.36 |
| 2004/0117004 A1 | 6/2004 | Osborne et al. | |
| 2004/0133273 A1 * | 7/2004 | Cox | A61F 2/2451 623/2.11 |
| 2004/0230293 A1 | 11/2004 | Yip et al. | |
| 2005/0038502 A1 | 2/2005 | Waysbeyn et al. | |
| 2006/0259131 A1 * | 11/2006 | Molaei | A61F 2/07 623/1.44 |
| 2007/0027526 A1 | 2/2007 | Demetriades et al. | |
| 2007/0135906 A1 | 6/2007 | Badylak et al. | |
| 2008/0243225 A1 * | 10/2008 | Satasiya et al. | 623/1.12 |
| 2009/0099642 A1 * | 4/2009 | Lerdahl | A61F 2/07 623/1.13 |
| 2009/0112237 A1 | 4/2009 | Paul, Jr. et al. | |
| 2009/0319023 A1 * | 12/2009 | Hildebrand et al. | 623/1.13 |
| 2010/0168837 A1 | 7/2010 | Magnuson et al. | |
| 2010/0262225 A1 * | 10/2010 | Schneider et al. | 623/1.15 |

FOREIGN PATENT DOCUMENTS

| | | |
|---|---|---|
| WO | WO 03/0053288 A1 | 7/2003 |
| WO | WO 2004/016201 A2 | 2/2004 |
| WO | WO 2005/048880 A2 | 6/2005 |
| WO | WO 2006/047520 A2 | 5/2006 |
| WO | WO 2007/134358 A2 | 11/2007 |

\* cited by examiner

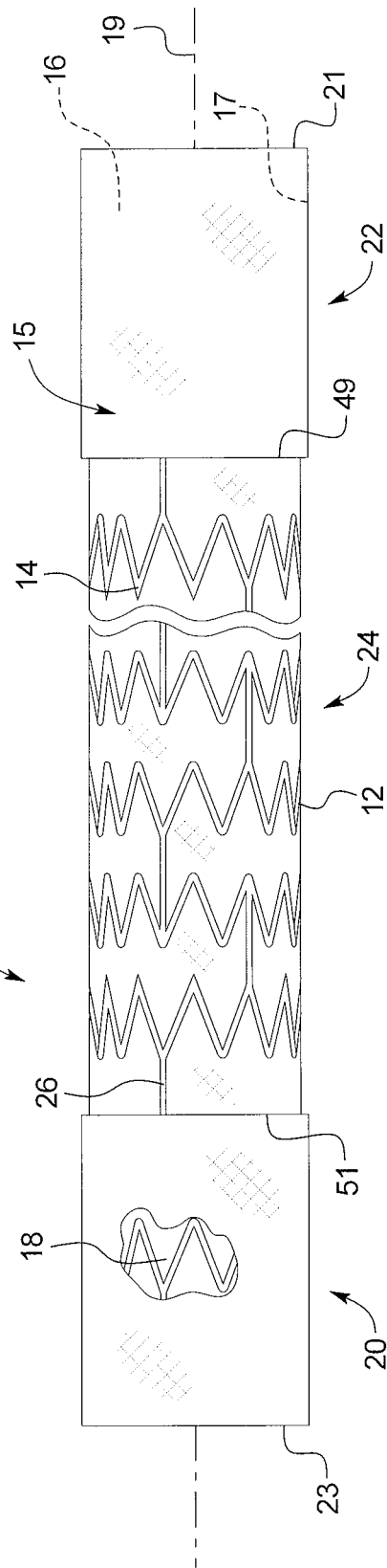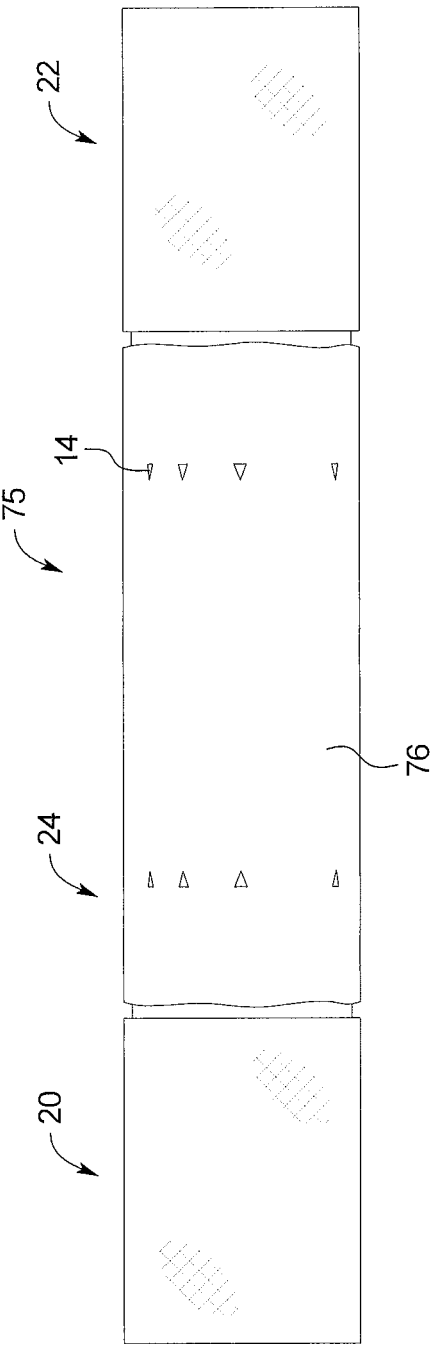

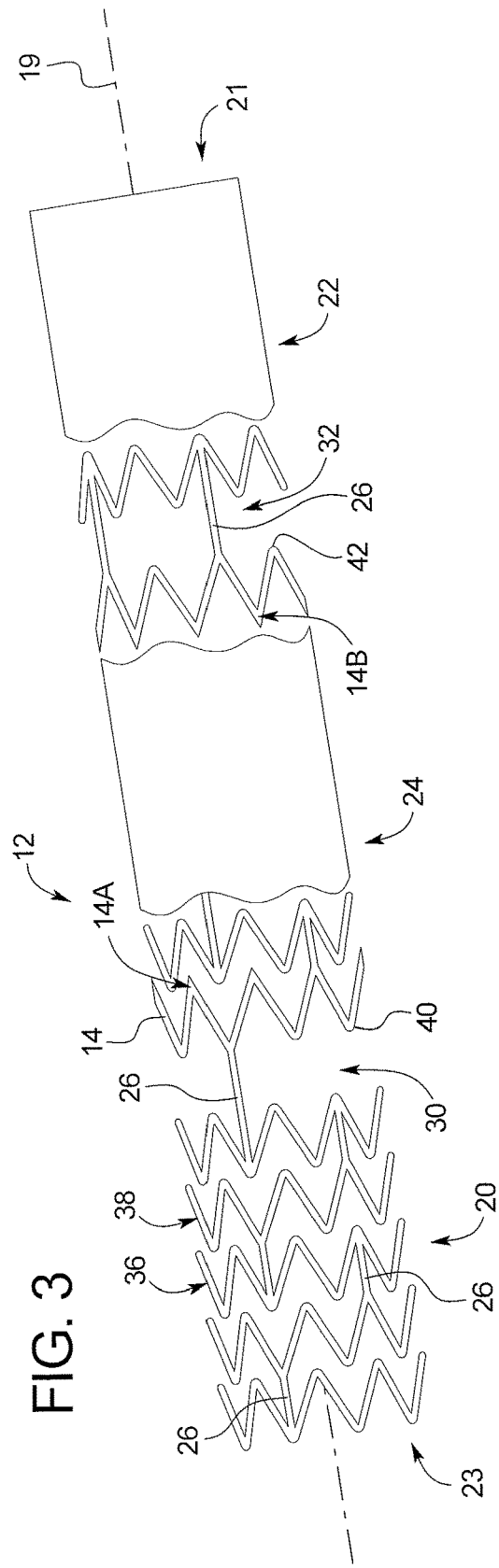
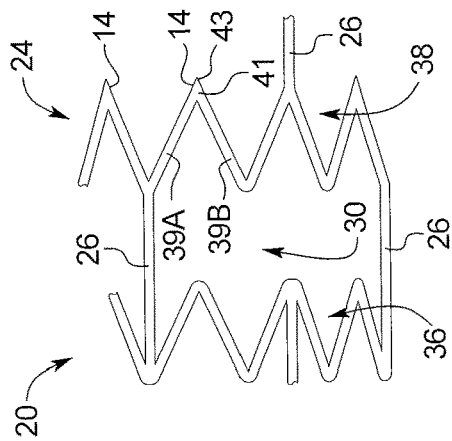
FIG. 3
FIG. 4A

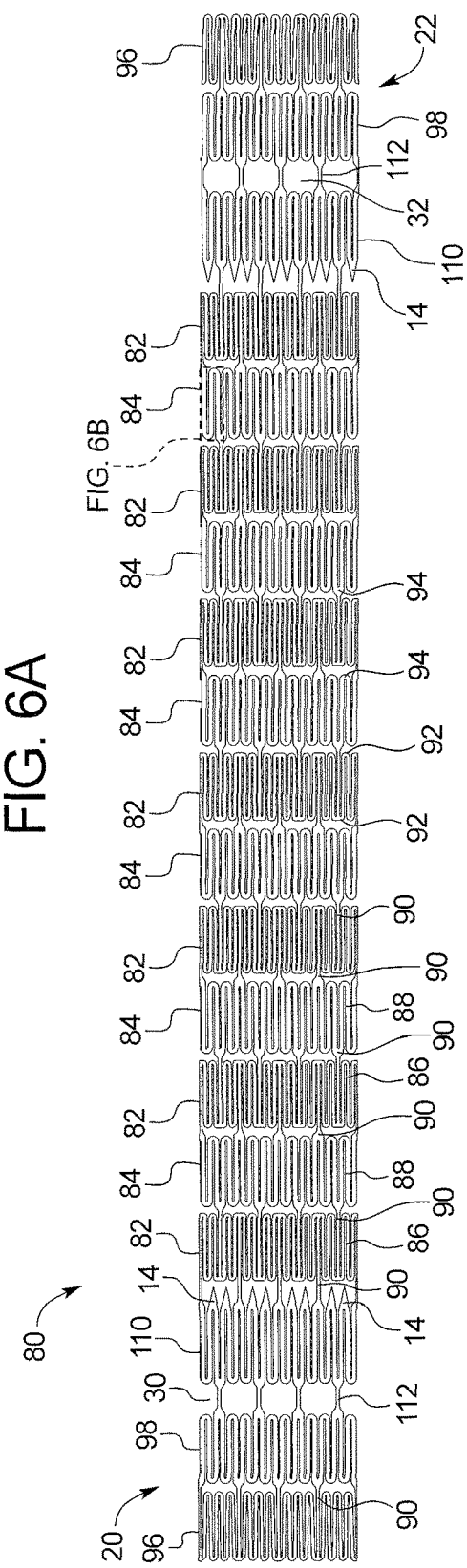
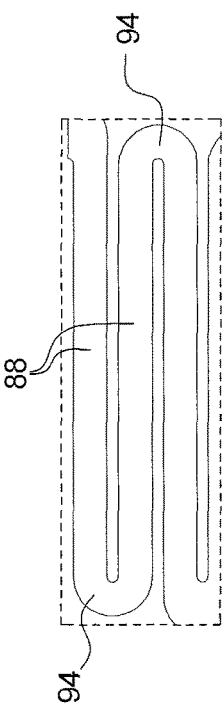

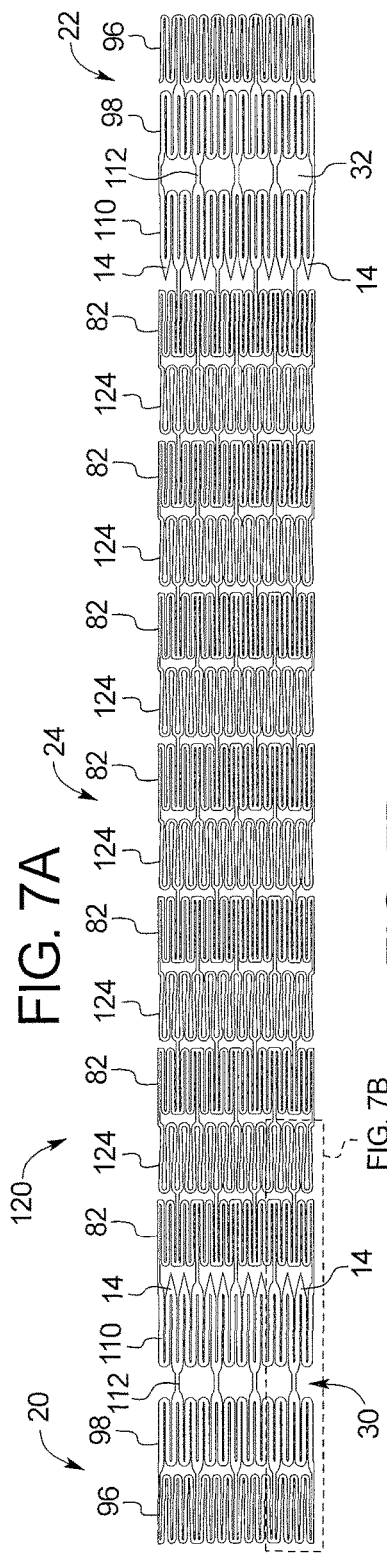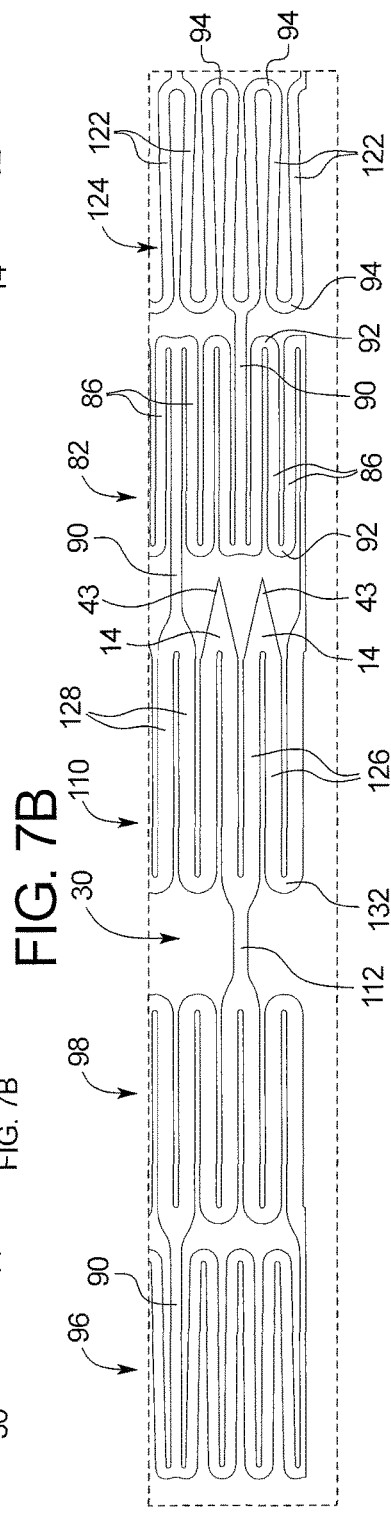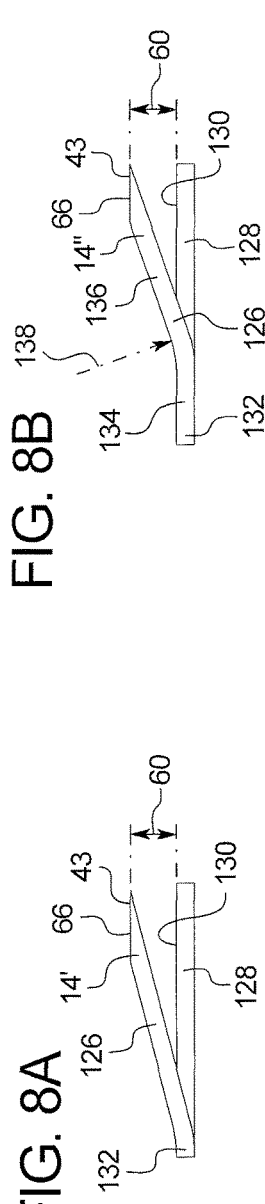

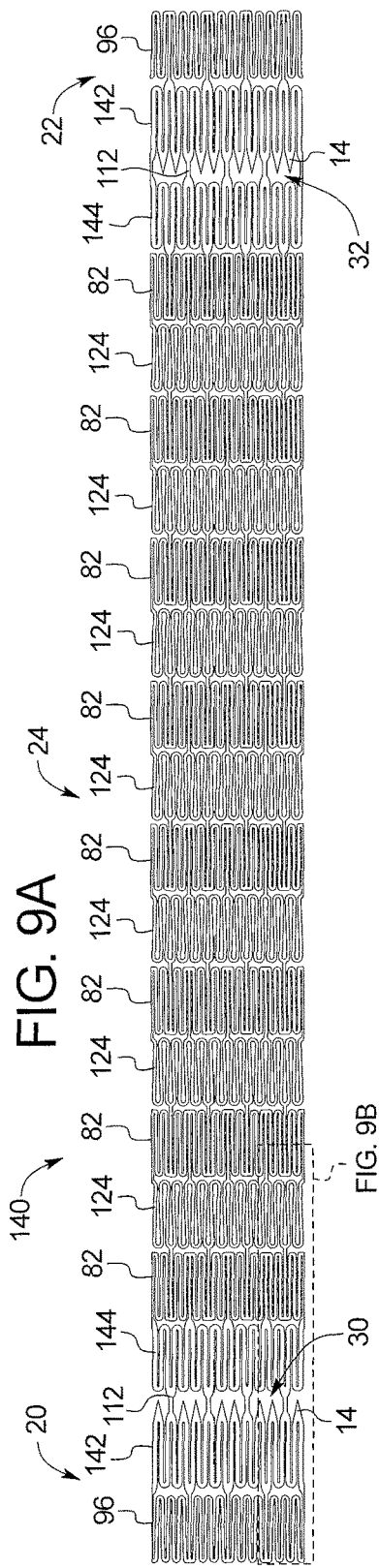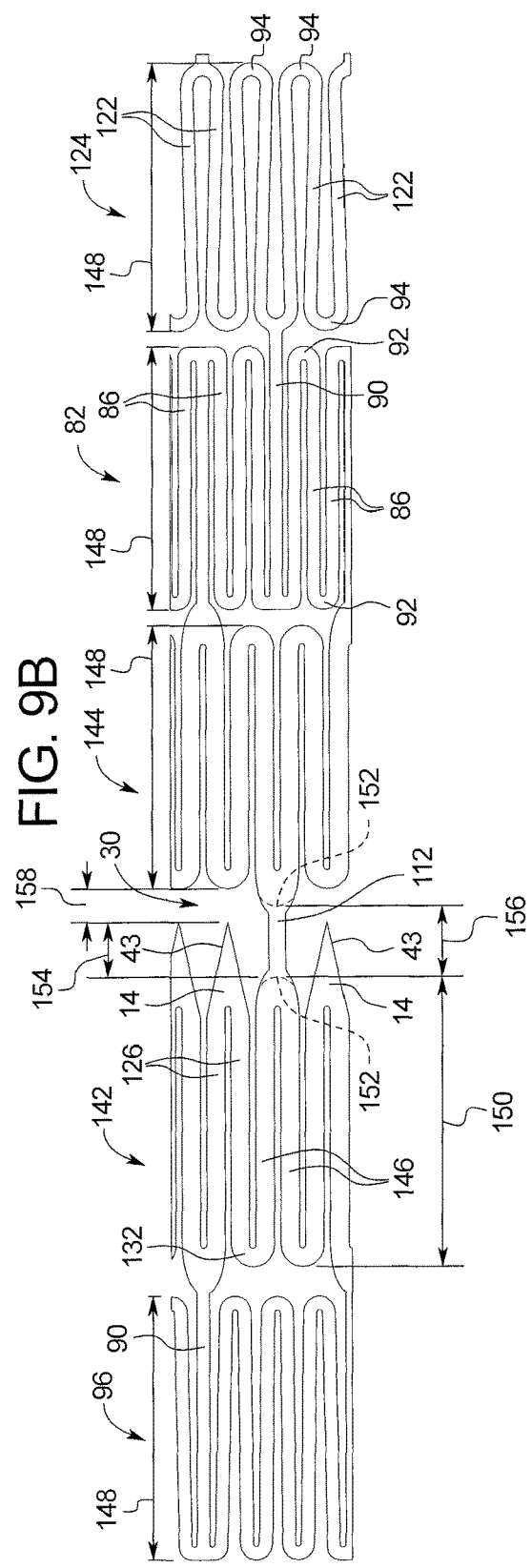

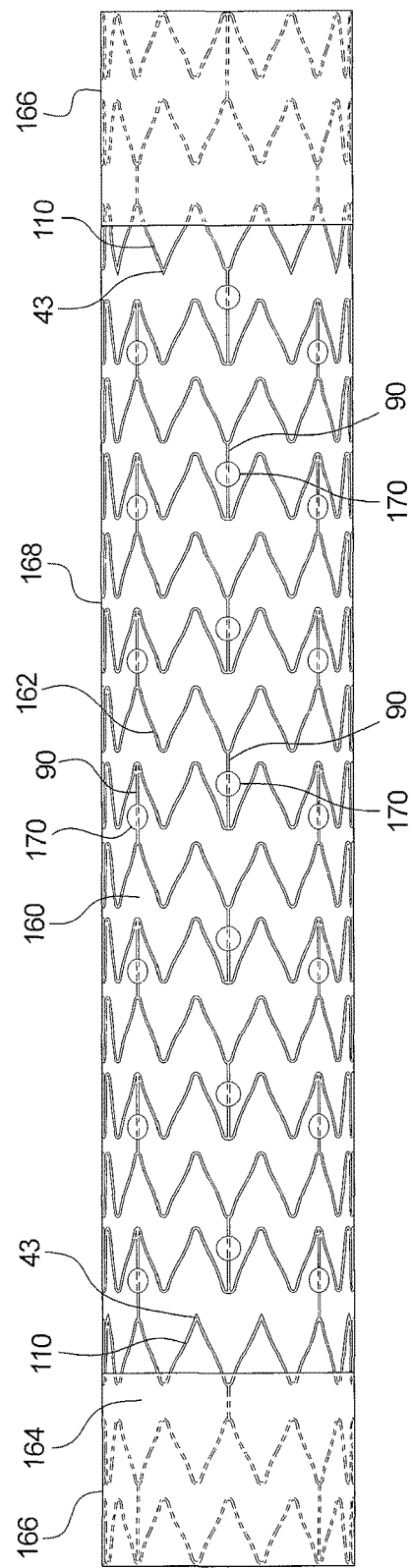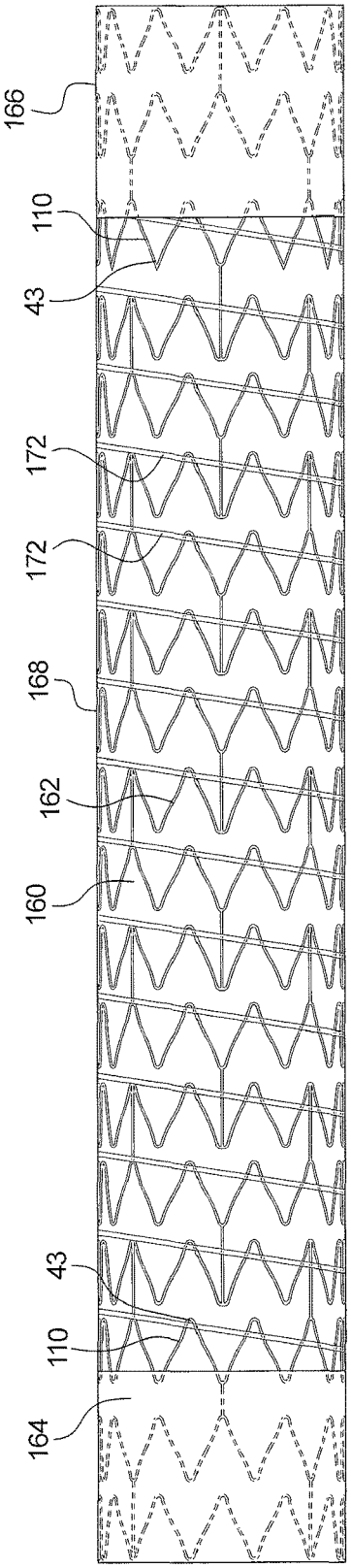

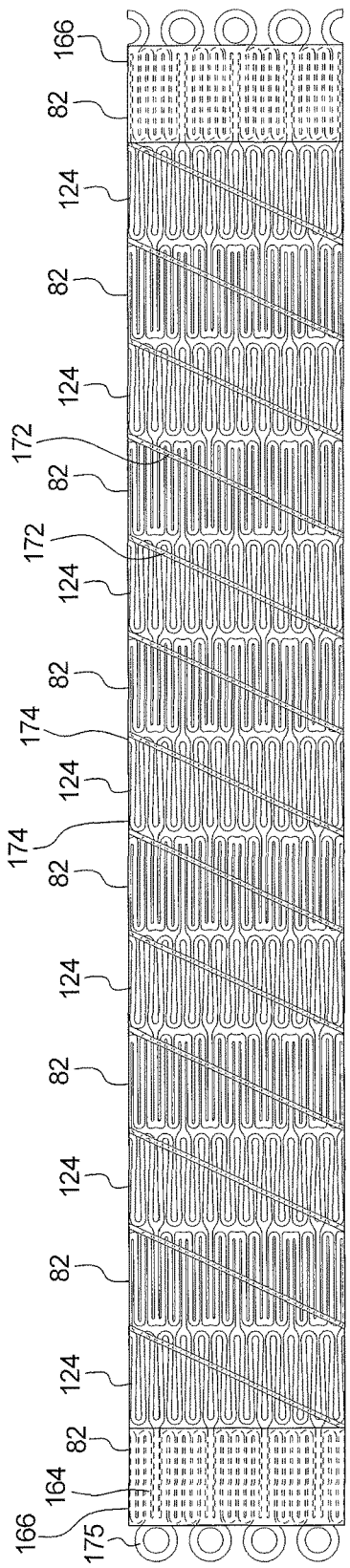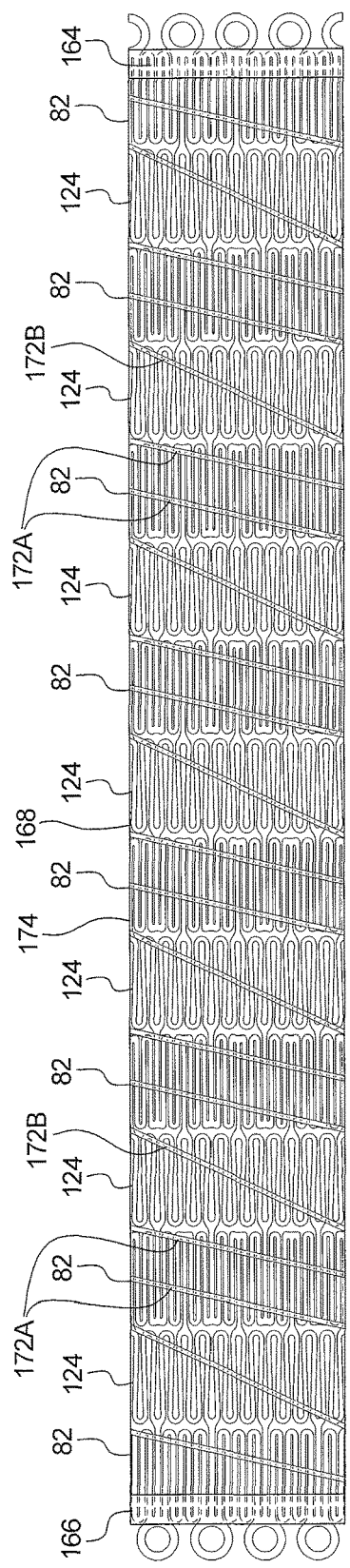

BLOOD PERFUSION DEVICE

This application is a continuation-in-part of U.S. patent application Ser. No. 13/197,511, filed Aug. 3, 2011, which claims priority to U.S. Provisional Application No. 61/370,304, filed Aug. 3, 2010, both of which are hereby incorporated by reference herein.

BACKGROUND

The preferred embodiments described herein relate generally to medical devices for repairing body vessels. More particularly, they relate to medical blood perfusion devices for repairing damaged body vessels and gaining hemostasis during emergency medical procedures.

Emergency or trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by emergency or trauma physicians to treat body vessel injuries include clamping the vessel with a hemostat, use of a balloon tamponade, ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the emergency physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. Ligation of the damaged blood vessel may result in muscle necrosis, loss of muscle function, or a potential limb loss or death.

Due to the nature of the body vessel injury that may be encountered, the use of shunts, repairing and/or ligating of a blood vessel often requires that such treatments be rapidly performed at great speed, and with a high degree of physician skill. Such treatments may occupy an undue amount of time and attention of the emergency physician at a time when other pressing issues regarding the patient's treatment require immediate attention. In addition, since the level of particularized skill required may exceed that possessed by the typical emergency physician, particularly traumatic episodes may require the skills of a physician specially trained to address the particular trauma, such as a vascular trauma, and to stabilize the patient in the best manner possible under the circumstances of the case.

U.S. Patent Publication No. 2007/0027526 A1, incorporated by reference herein in its entirety, discloses a device for repair of damaged portions of a body vessel. One device depicted in FIG. 1 of the patent publication includes a cylindrical conduit body 12, having a fitting 14 disposed at either or both axial ends of the cylindrical body. This device is suitable for placement within a blood vessel for repair of vascular trauma and restoration of blood flow through the vessel. One end of the fitting can be snugly received within the lumen of the cylindrical body, and one or more sutures 18 can be tied around the circumference of the cylindrical body to secure the fitting firmly to the cylindrical body along a first recess. When the device is positioned in the vessel undergoing repair, one or more sutures 20 are tied around the vessel at an exposed portion of the fitting along a second recess 16, as shown in FIG. 5, to secure the vessel to the fitting. The device depicted in the 2007/0027526 A1 publication is believed to be effective in repairing damaged vessels utilizing open surgical techniques in an emergency situation. However, since the device utilizes sutures to affix the damaged tissue portions to the fitting, the emergency physician must take time to tie the sutures properly. Although in modern medicine sutures can be tied in relatively rapid fashion, any step in a repair process that occupies physician time in an emergency situation is potentially problematic. Therefore, efforts continue to develop techniques that reduce the physician time required for such techniques, so that this time can be spent on other potentially life-saving measures.

In addition to the foregoing, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel.

Another device 40 is depicted in FIG. 6 in the 2007/0027526 A1 publication and includes an expandable cylindrical body 44, having a fabric graft 45 covering the stent body. Barbs 43 can be provided along a portion of the circumference of the stent body to anchor the device into the vessel, and are shown extending through the fabric graft. Device 40 can be delivered with a conventional delivery sheath 42 as shown in FIGS. 8-10.

U.S. Patent Publication No. 2005/0038502 A1 describes a docking head that is mounted on a graft having an outer diameter so as to couple the graft to a blood vessel without requiring the use of sutures. The docking head includes a hollow truncated cone having a passage that is adapted to correspond to the outer diameter of a graft and a plurality of outwardly pointing and inclined barbs. The barbs may be flexible and inclined opposite a truncated end of the hollow truncated cone and are 1 to 4 times the thickness of the wall of the blood vessel. The inclined barbs are arranged at the circumference of the conical structure in at least one row and are distally pointed to the direction of the graft's body. In operation, the conical structure followed by the graft is inserted into neck through its narrow end while inclined barbs smoothly pass through a portion of the neck. Upon pulling back the conical structure, inclined barbs are embedded within the neck, forming a firm and sealed connection between the vessel and the graft.

While the outward facing barbs may facilitate secure placement of graft by securing the truncated cone portion within a body vessel, the particular design of the outward facing barbs presents drawbacks. First, these inclined barbs extending from the outer surface of the docking head, for example as shown in FIGS. 14 and 15, may engage body tissue away from the intended point of treatment during placement of the device. The tendency of the barbs pointing outwardly to engage tissue or other surfaces inadvertently can present a challenge during emplacement of the graft. Second, once in place within a body vessel, these barbs are not sized to penetrate an optimal distance into the wall of the body vessel. For example, FIG. 19 shows barbs 404 penetrating through the entire wall of a body vessel, which can lead to undesirable complications, such as bleeding and/or thrombus formation.

Emergency physicians generally know how to use a stent delivery catheter. Accordingly, when encountering patients having traumatic injury to a body vessel, it would be desirable for the emergency physician to deliver a medical device with a conventional stent delivery catheter to repair the injured body vessel. Thus, it would be desirable to provide a device for use in repair of an injured body vessel, such as an artery or a vein, during emergency surgery in a manner that is time effective, that addresses the trauma at hand to the extent possible, and that utilizes techniques that may be readily practiced by an emergency physician. In addition, it would be desirable if the device utilized during emergency surgery can be permanently placed within the patient, thereby obviating a need for subsequent surgical intervention. It is also desirable to provide a medical device having inclined barbs that are shielded from inadvertent contact with body tissue by a delivery system during the delivery process, and/or barbs adapted to penetrate only a portion of the wall of the body vessel required to secure the medical device within the body vessel.

SUMMARY

A perfusion device and system for repair of a damaged portion of a body vessel are provided. The device can be a vascular conduit for use in repair of the body vessel, such as an artery or a vein, during emergency surgery in a manner that is time effective to rapidly gain hemostasis, that addresses the trauma at hand to the extent possible, and that utilizes techniques that may be readily practiced by an emergency or trauma physician. The device utilized during emergency surgery can be permanently placed within the patient, thereby obviating a need for subsequent surgical intervention. Since the body vessel has a vessel wall including a tunica intima, a tunica media, and a tunica adventitia, the device controllably interacts with the tunica intima, basement membrane, and tunica media, and avoids interaction with the tunica adventitia to not disrupt the vasa vasorum residing in the tunica adventitia. The device is preferably secured in a rapid manner without the use of a ligature or suture placed around the vessel.

The perfusion device can be a vascular conduit having a tubular body that is radially self-expandable from a compressed configuration to an expanded configuration in order to be positioned along the vessel wall. The tubular body has a proximal end and a distal end and defines a lumen about a longitudinal axis. The tubular body can include a proximal portion, a distal portion, and an intermediate portion, with each portion including a plurality of struts and bends interconnecting the struts. Each of the distal and proximal portions is preferably axially spaced from the intermediate portion by a first gap and a second gap, respectively. The intermediate portion has a proximal end adjacent the first gap and a distal end adjacent the second gap. A series of barbs, preferably distally facing barbs, can be disposed circumferentially along the proximal end of the intermediate portion. Another series of barbs, preferably proximally facing, can be disposed circumferentially along the distal end of the intermediate portion. Barbs are capable of penetrating into the tunica intima and tunica media of said vessel wall upon insertion of said device into said body vessel, and not into said tunica adventitia to help anchor the vascular conduit to the vessel wall in order to inhibit migration within the vessel. A graft covering can be associated with the tubular body. The graft covering has a proximal end and a distal end, and preferably extends entirely along a luminal wall of the tubular body to inhibit the blood from leaving through the laceration. The graft covering may also extend along an exterior surface of the tubular body at the proximal and distal portions so that the exterior surface along the intermediate portion is left uncovered. To this end, in one example, the exterior surface of intermediate portion can be left with bare conduit material facing the vessel wall and laceration, which can stimulate endothelial cell growth for healing along this portion. The ends of the vascular conduit may also include graft material to seal the edges of the vascular conduit and direct any blood flow through the vascular conduit lumen. In another example, the exterior surface of the intermediate portion of the vascular conduit may also have a graft covering in the form of a remodelable material that is to be positioned in close proximity to the vascular injury and act as a remodelable surface to enhance cell growth and healing. In yet another example, a removable sleeve can be disposed to surround and retain the entire vascular conduit in the compressed configuration. In one aspect, the removable sleeve can be dissolved with an activation agent. In another aspect, the removable sleeve can be peeled away from the vascular conduit, for example, peeled away from the middle of the conduit.

Barbs can include a first strut interconnected to a second strut by one of the bends of the intermediate portion, with a barb tip extending outward from the bend. Barbs can have a length of about 0.1 mm to about 1 mm. A portion of the barb base can be rounded or have a dullness to inhibit cutting radially. The barb tip can be generally parallel with the longitudinal axis or have a surface that is generally parallel with the longitudinal axis when in the deployed configuration. Barbs may also have a delivery configuration when the tubular body is in the compressed configuration and a deployed configuration when the tubular body is in the expanded configuration. When in the delivery configuration, the barbs are preferably substantially parallel to the longitudinal axis. When in the deployed configuration, the barbs can extend radially outward at an angle of about 5 degrees to about 30 degrees relative to the longitudinal axis.

The delivery system includes a delivery device and a vascular conduit according to one of the embodiments. The delivery device can include an outer sheath and an inner catheter. The distal portion of each of the outer sheath and the inner catheter can be sized to receive the vascular conduit that is in the radially compressed configuration. A handle having a cylindrical body and a pushrod sized to be received in the cylindrical body can also be provided. The cylindrical body can be coupled to the outer sheath and the pushrod can be coupled to the inner catheter so that relative movement between the cylindrical body and the pushrod can cause the outer sheath to move relative to the inner catheter. With this relative movement, the vascular conduit is capable of moving to the radially expanded configuration for deployment against the body vessel.

A method of repairing a laceration in a damaged body vessel is also provided. The method can include one or more of the following steps: forming an opening in the damaged body vessel wall that is axially spaced from the laceration; introducing a delivery system through the opening, the delivery system comprising a delivery device and a vascular conduit; translating the delivery system through the damaged body vessel until the intermediate portion of the vascular conduit can be positioned to span across the laceration; and moving the outer sheath of the delivery device from the vascular conduit so that the vascular conduit radially expands against the laceration of the damaged body vessel.

In another example, when the vascular conduit includes a removable sleeve that is everted such that the first and second ends are gathered toward a middle of the sleeve, the delivery device can include a body and a lever attached to the body. The body can have a distal tip to contact a center of the removable sleeve. The lever can be configured to retain the first and second ends of the sleeve, and movable away from the distal tip of the delivery device body to cause eversion of the removable sleeve away from the ends of the vascular conduit. Here, the vascular conduit can be inserted through the laceration into the body vessel. The vascular conduit can be attached to the delivery device body by retaining the ends of the sleeve to the lever. The lever can be moved relative to the distal tip for eversion of the sleeve from the ends toward the center. As the lever is moved, the sleeve continues to split, thereby removing the retaining force away from the vascular conduit so that it can radially expand.

Yet, in another example, when the vascular conduit includes a removable sleeve that is dissolvable with an activation agent, the vascular conduit can be inserted through the laceration into the body vessel and positioned suitably for treatment. Activation agent can then be applied to the sleeve, usually with a syringe, to commence the dissolving process. Once the sleeve loses is retaining forces from the vascular conduit because of the dissolving process so that the vascular conduit can radially expand.

BRIEF DESCRIPTIONS OF THE DRAWINGS

FIG. 2 is an elevation view of a vascular conduit according to one of the described embodiments, in a radially expanded configuration.

FIG. 3 is an elevation view of the vascular conduit of FIG. 2, depicting a portion of the body of the vascular conduit without a graft covering.

FIG. 4A is an enlarged partial elevation view of the body of a vascular conduit, depicting a gap.

FIG. 5 is an elevation view of an alternative vascular conduit, in a radially expanded configuration.

FIG. 6A is a plan view of the body of a vascular conduit according to another of the described embodiments, in an unrolled configuration.

FIG. 6B is an enlarged plan view of a portion of the vascular conduit in FIG. 6A.

FIG. 7A is a plan view of the body of a vascular conduit according to another of the described embodiments, in an unrolled configuration.

FIG. 7B is an enlarged plan view of a portion of the vascular conduit in FIG. 7A.

FIG. 8A is an enlarged elevation view of a barb of the vascular conduits.

FIG. 8B is an enlarged elevation view of another barb of the vascular conduits.

FIG. 9A is a plan view of the body of a vascular conduit according to another of the described embodiments, in an unrolled configuration.

FIG. 9B is an enlarged plan view of a portion of the vascular conduit in FIG. 9A.

FIG. 10 is a side view of a vascular conduit with one embodiment of a graft.

FIG. 11 is a side view of a vascular conduit with another embodiment of a graft.

FIG. 12 is a side view of a vascular conduit with another embodiment of a graft.

FIG. 13 is a side view of a vascular conduit with another embodiment of a graft.

DETAILED DESCRIPTION OF THE DRAWINGS AND THE PRESENTLY PREFERRED EMBODIMENTS

Figure 1:
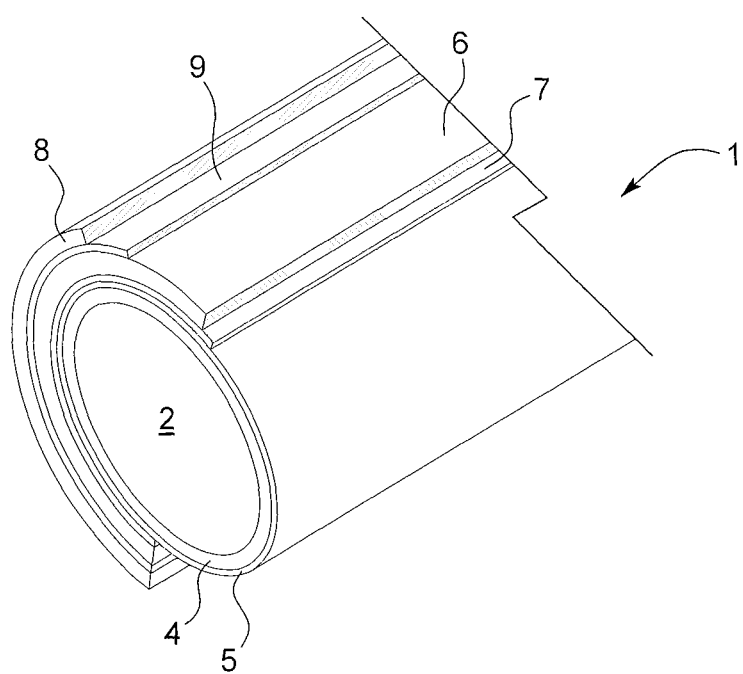
FIG. 1 is a sectional view of a blood vessel that schematically illustrates the orientation of the layers of the blood vessel.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Delivery devices and methods of repairing body vessels that may be used in conjunction with the devices described herein are described in U.S. Ser. No. 13/197,074, filed on Aug. 3, 2011 by Paul, Jr. et al. entitled Blood Perfusion Device Delivery System, which is incorporated herein by reference in its entirety.

The device of the presently described embodiments can be useful for repair of a body vessel, such as a blood vessel, during an emergency open surgical procedure. This device can be particularly useful for repair of a lacerated artery or vein during emergency surgery, and particularly, to obtain hemostasis while maintaining blood perfusion. While some devices are only implanted temporarily for treatment, this device can be implanted permanently thereby obviating the need for further surgical intervention and repair.

In order to understand the structure and operation of the inventive device, a brief description of the structure of a blood vessel in the body is helpful. Blood vessels are of two types, namely arteries and veins. Generally speaking, arteries are elastic vessels that carry oxygenated blood away from the heart, and veins are elastic vessels that transport blood to the heart that then transport blood to the lungs for oxygenation. The walls of both arteries and veins generally consist of three layers or tunics. The inner layer is referred to as the tunica intima, which is composed of endothelium and delicate collagenous tissue. The middle layer is referred to as the tunica media, which is composed of typically a muscular layer, and consists of smooth muscle and elastic fibers. The outer layer is referred to as the tunica adventitia, which is the outer covering of the vessel, and is composed of connective tissue, collagen, and elastic fibers. The tunic adventitia includes small vessels, referred to as vasa vasorum, which supply nutrients to the tissue.

FIG. 1 is a sectional view of a blood vessel 1 that schematically illustrates the orientation of these layers. Vessel 1 includes a lumen 2 extending therethrough for transport of blood. The respective tunica intima 4, tunica media 6, and tunica adventitia 8 extend radially outwardly from the lumen 2. The tunica intima 4 includes a thin layer of connective tissue 5 (often referred to as the basement membrane) in the region where it joins the tunica media 6. A thin layer of internal elastic lamina 7 may also be found between the tunica intima 4 and the tunica media 6. Another thin layer of external elastic lamina 9 may also be found between the tunica media 6 and the tunic adventitia 8. The illustration and accompanying explanation provided hereinabove is only intended to be a very brief explanation of the structure of a blood vessel. Those skilled in the art will appreciate that the relative thickness of a particular layer will vary from that shown schematically in FIG. 1, and that the thickness of various layers will also vary depending upon whether the vessel is an artery or a vein. In each instance, however, the vessel should include the three layers illustrated in FIG. 1. It is believed that those skilled in the art will have sufficient appreciation for the basic vessel structure that further explanation is unnecessary to achieve an understanding of the present invention.

FIG. 2 illustrates one embodiment of an inventive vascular conduit 10 that can include a generally tubular conduit body 12, a plurality of barbs 14 along a portion of conduit body 12, and a graft covering 15. Conduit body 12 can be expandable between a radially compressed, delivery configuration to a radially expanded, deployed configuration (as shown in FIG. 2). Graft covering 15 can extend along a luminal wall 17 of conduit body 12, and along a portion of an exterior surface 18 of conduit body 12. Vascular conduit 10 has a size and shape suitable for placement within a body vessel, such as an artery or vein, and most particularly, for placement at the site of a vascular trauma.

Conduit body 12 defines a lumen 16 about a longitudinal axis 19, between a distal end 21 and a proximal end 23 of conduit body 12. Conduit body 12 can have a substantially circular cross-section having any outer diameter in the expanded configuration suitable for body vessels, such as about 5 mm or greater, to engage the luminal surface of the body vessel wall. Although a substantially circular cross-section is generally preferred, the cross-section of the body may be elliptical or other shapes known by one skilled in the art to be used in a body vessel. The general length of conduit body 12 will depend upon the size of the laceration or puncture wound opening in the vessel. The length of conduit body 12 is at least as long as the laceration in the vessel, if not longer, in order for barbs 14 to penetrate and engage securely to an uncompromised portion of the vessel.

The conduit body can be any pattern of stent structures in the art, although the conduit body in FIGS. 2-3, for example, is designed primarily for its intended purpose. Conduit body 12 can be composed of a proximal portion 20, a distal portion 22, and an intermediate portion 24 connected to the proximal and distal portions 20, 22 by a plurality of axial struts 26. Intermediate portion 24 is preferably positioned along the laceration. Proximal portion 20 can be axially spaced from intermediate portion 24 by a first gap 30, while distal portion 22 can be axially spaced from intermediate portion 24 by a second gap 32. The gaps can be annular gaps with one or more longitudinal struts spanning the gap in order to connect the distal and proximal portions to the intermediate portion. The longitudinal length of the proximal and distal portions 20, 22 can be same length, or may even be different as appreciated by those skilled in the art.

Each of portions 20, 22, 24 can include a repeating series of first and second alternating segment types. A first segment type 36 can be connected to a second segment type 38 by axial struts 26. First segment type 36 comprises a plurality of struts interconnected to one another by bends to form a zigzag pattern. Second segment type 38 comprises a plurality of struts interconnected to one another by bends to form a zigzag pattern. Axial struts 26 can be arranged peak-to-peak or valley-to-valley of the zigzag pattern to connect the first and second segment types 36, 38. The strut thickness of first segment 36 may be less than the strut thickness of second segment 38. FIG. 4A depicts a partial exploded view of first gap 30 being surrounded by segment types 36, 38. Barb 14 can be located at a bend 41 connecting a first strut 39A to a second strut 39B.

Figure 3A:
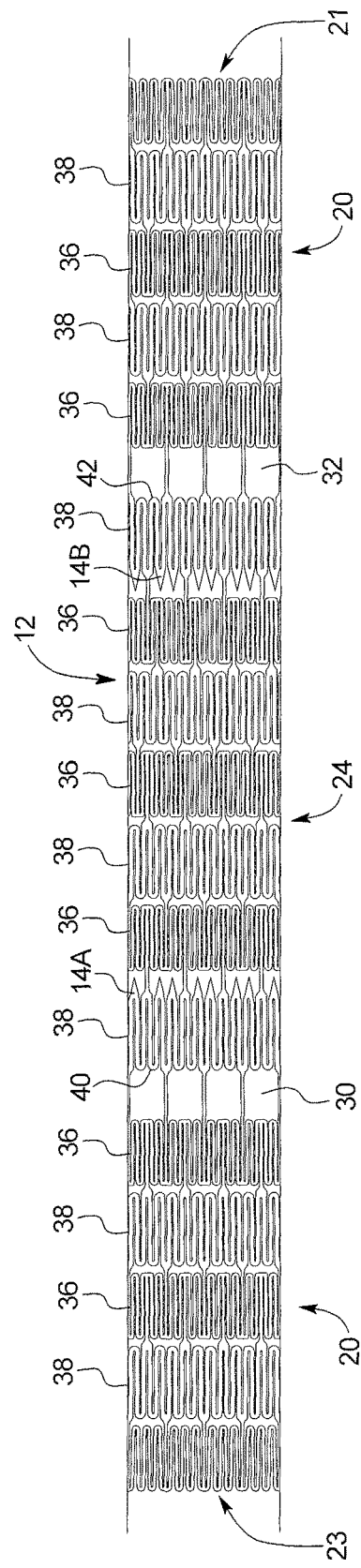
FIG. 3A is a plan view of the body of the vascular conduit in FIG. 3, in an unrolled configuration.

Conduit body 12 can be formed of a biocompatible metal, such as stainless steel (e.g., 316L SS), titanium, tantalum, nitinol or other shape memory materials, or a high-strength polymer. To form the alternating longitudinal segments from a metal cannula or sheet, material must be removed in some manner, such as by commercially available computer-controlled laser, leaving a framework of integrated support members that has a small surface area relative to the initial surface area of the cannula or sheet. Other methods of manufacture include chemical etching, machining, electrode discharge machining or cutting with a water jet. Finishing techniques can also be used to remove some material, e.g., electropolishing or grinding. FIG. 3A depicts conduit body 12 as a laser cut cannula of material that has been flattened out for illustrative purposes.

Referring back to FIG. 3, intermediate portion 24 can include a proximal end 40 adjacent first gap 30 and a distal end 42 adjacent second gap 32. Barbs 14 can be disposed along any portion of conduit body 12, but are preferably disposed along intermediate portion 24. A first series 14A of barbs 14 can point toward distal end 21, and a second series 14B of barbs 14 can point in the opposite direction toward proximal end 23. Series 14A, 14B of barbs may even form a first ring and a second ring of barbs around the body proximate proximal and distal ends 40, 42, respectively. First and second series 14A, 14B of barbs can be spaced longitudinally apart from one another so that the barbs bound the vessel laceration or treatment site. It can be appreciated by those skilled in the art that the barbs 14 need not form a ring as shown, but can be arranged in other patterns so long as a portions of barbs bound the vessel injury. It is desirable to have the alternating segment types of intermediate portion 24 to define cells that are sufficiently sized to promote endothelial cell growth for coating the struts and bends of the intermediate portion.

The presence of barbs 14 permits vascular conduit 10 to be secured to the tissue of the vessel during a medical procedure. In particular, barbs 14 provide vessel fixation while avoiding adverse conditions associated with disturbing the vasa vasorum and/or pressure induced necrosis of the medium muscular arteries of the type that may result from tying ligatures circumferentially around a connector or a vascular conduit. Barbs 14 can further include various shaped member structures, including fibers, bristles, or outer protruding and penetrable media. It is noted that the barbs in the Figures are enlarged in order to illustrate the general shape of the barbs and may not accurately reflect the true size of the barbs in relation to the vascular conduit or connector.

Barbs 14 can be sized and shaped in any manner to enable a secure connection with the vessel that is sufficient to inhibit migration of vascular conduit 10 within the vessel. It is desirable, however, that barbs 14 are sized and shaped such that they may penetrate the tunica intima 4, the basement membrane 5, and partially enter the tunica media 6 (FIG. 1). It is preferable that any portion of barbs 14 do not enter the tunica adventitia, and more importantly, do not disturb or otherwise adversely affect the vasa vasorum. A fibrotic response can be created within the penetrated portions of the blood vessel, which further anchors vascular conduit 10 in the vessel over time. Alternatively, the barbs 14 may only partially penetrate the vessel layers and/or may only apply outward pressure against some or all of the layers.

A wide variety of configurations for barbs 14 are provided in order to better secure vascular conduit 10 with the tissue. Barbs 14 can be constructed to have varying dimensions, such as length, base width, thickness, barb angle, orientation, distribution, sharpness, and point (tip) configuration. These dimensional configurations can aid in selecting the degree of penetration into the vessel wall, and preferably, to restrict penetration through only the tunica intima and partially into the tunica media layers as described. For example, barbs 14 may be configured to penetrate the wall of the body vessel without cutting through the body vessel. In other examples, barbs 14 can be also configured to seat within the body vessel wall securely as to not further propagate or cut radially once engaged.

Figure 4C:
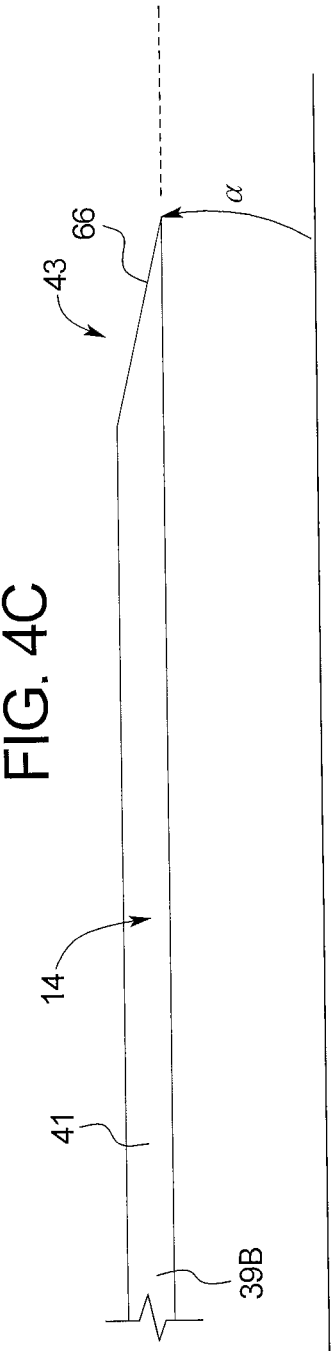
FIG. 4C is an enlarged elevation view of a barb of the vascular conduit in FIG. 2, in a delivery configuration.
Figure 4B:
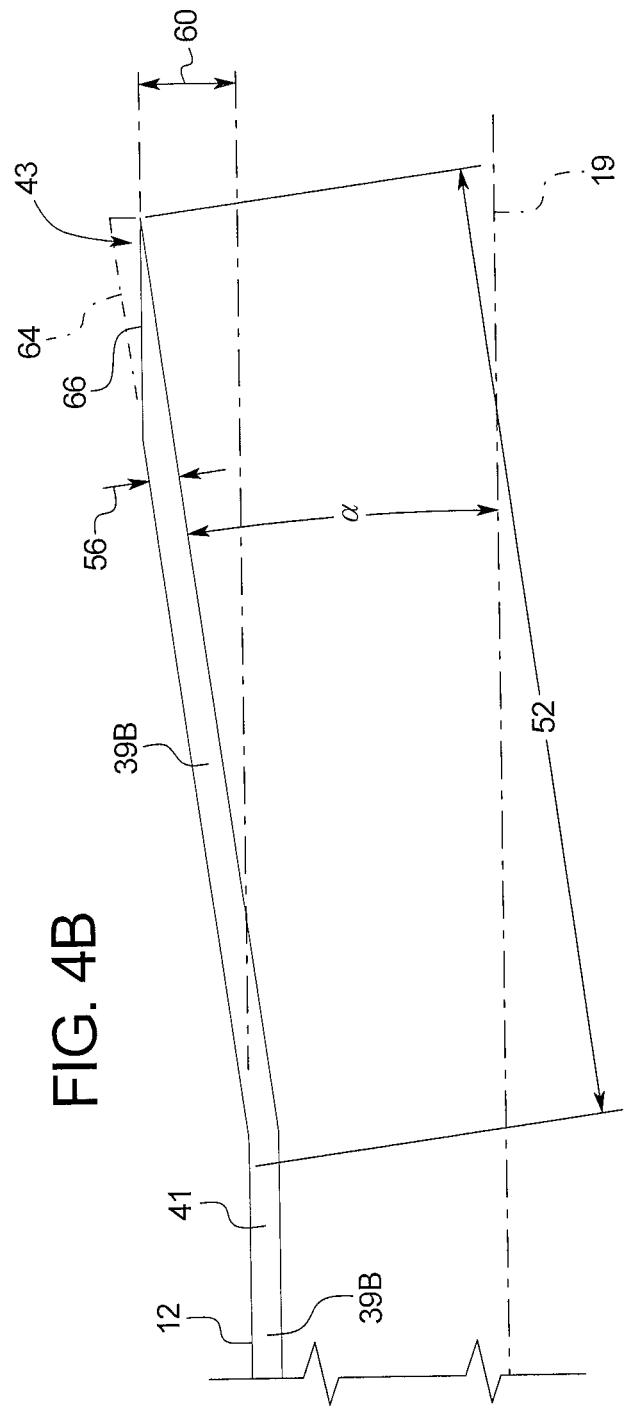
FIG. 4B is an enlarged elevation view of a barb of the vascular conduit in FIG. 2, in a deployed configuration.
Figure 4D:
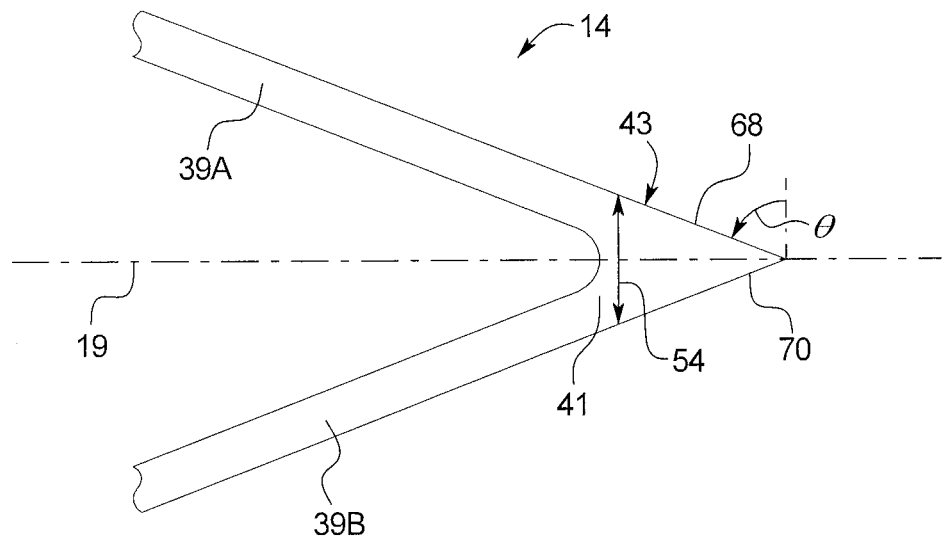
FIG. 4D is an enlarged plan view of a barb of the vascular conduit in FIG. 2, in a deployed configuration.

Referring to FIGS. 4B-4D, the general length 52, angle α, base width 54 and thickness 56 of barb 14 can vary depending on the vessel type and characteristics. For example, for a vascular conduit 10 having an outer diameter of 6 mm, barbs 14 can have a length 52 in the range between about 0.1 mm to 1 mm, and preferably about 1 mm, where the length is measured from intersection of the base of the barb 14 with the bend 41 to the barb tip 43. Base width 54 typically depends on the size of the bends and strut thickness. The number of barbs 14 can have a range from about 2 to about 20, although any number suitable for implantation of the vascular conduit is within the scope. As a result, base width 54 can be in the range between about 0.2 mm or less to about 0.4 mm or more, such as 0.8 mm.

Referring to FIG. 4B, the angle α of barb 14 in the deployed configuration is preferably selected to orient barb 14 radially outward away from longitudinal axis 19 in a manner to prevent penetration into the tunica adventitia. Optionally, barb 14 may be configured to penetrate at a certain depth 60 into the vessel wall as to avoid the tunic adventitia. Although it is preferable that all of barbs 14 have a substantially similar angle α, or similar depth 60 penetration, it can be appreciated by one skilled in the art that barbs 14 having varying angles, or depth penetrations 60, may be advantageous. Angle α of about 5 degrees to about 30 degrees is preferred, although an angle of up to about 45 degrees to 60 degrees may also be used in some applications depending on the length 52 of the barb and the preferred depth 60 penetration. For example, angle α of barb 14 may be oriented at about 20 degrees to about 30 degrees, and most preferably at about 25 degrees. The suitable barb length, angle, and/or depth penetration can be determined by the vessel type and other considerations taken into account by one of ordinary skill in the art.

Barbs 14 can move between a delivery configuration and a deployed configuration. For instance, when conduit body 12 is in the radially compressed configuration, as shown in FIG. 4C, barbs 14 are surprisingly in substantial alignment with longitudinal axis 19. Otherwise, the barbs would still be extending radially outward when the conduit body is in the radially compressed configuration, resulting in an increased risk that the barbs may be compromised or damaged during delivery or extend through a delivery sleeve. This arrangement can facilitate delivery of the vascular conduit as the barbs are in a location to not interfere with an outer catheter wall during its relative movement for delivery. During radial expansion of conduit body 12 to the radially expanded configuration, barbs 14 can pivot radially outward to the deployed configuration, which is shown in FIG. 4B. It is preferable that only barbs 14 and the region generally around it extend radially outward instead of the barbs and first and second struts 39A, 39B. To this end, the vascular conduit is generally cylindrical with the barbs engaging into the body vessel. When struts 39A, 39B also extend outward, there is an increased risk of irritation to the body vessel, as well as pockets formed from the separation of the body vessel from the vascular conduit body.

Tip 43 of barbs 14 may be formed by one or more angled cuts to create a bi-angled tip, as shown in FIG. 4D. The cuts forming tip 43 can have edges 68, 70 that may be cut at different or the same angle Θ. Angle Θ may range from about 15 degrees to about 60 degrees relative to longitudinal axis 19, although the angle Θ for one edge of edges 68, 70 can be substantially parallel to longitudinal axis 19. Edges 68, 70 can be rounded, or otherwise made dull, to decrease the risk of the edges from cutting radially within the body vessel tissue once engaged. Techniques for making edges 68, 70 rounded and dull can be by abrasive treatment, chemical treatment, abrasive blasting, and/or electropolishing. It is preferred to have tip 43 with a complex-angle, where, when barb 14 is angled at a predetermined angle α, tip 43 has a surface 66 generally parallel to the longitudinal axis 19, as shown in FIG. 4B. Surface 66 can be formed by removing a portion 64, represented by the dashed lines, from the tip. Although removed portion 64 is shown to be at the outward surface of tip 43, the inner surface of tip 43 can instead be ground to create a surface generally parallel. Alternatively, surface 66 may be arcuate after being ground to be concave outwardly or inwardly depending on which side of the tip is ground. This can allow barb tip 43 to be sharpened without sharpening edges 68, 70 along the length of barbs 14. Optionally, instead of removing portion 64, a distal portion may be formed by forming barb 14 with a bent portion at tip 43, or by bending barb 14 at tip 43, to create a surface or portion that is substantially parallel to the longitudinal axis 19. Surface 66 or bent portion can allow for easier penetration into the wall of the vessel to a limited depth 60 or distance into the innermost layer(s) of the body vessel wall, without passing through the body vessel.

Barbs 14 may have a region, preferably along its tip 43, with a controlled porosity to allow for tissue in-growth as well as delivery of drugs or growth factors and other tissue modulators. For example, collagen-based formulations can be used to provide a growth and attachment matrix. There can also be features (e.g., bioremodelable materials, such as SIS) placed strategically around the cylindrical conduit body 12 and/or barbs 14 of the vascular conduit 10 to promote tissue attachment.

Barbs 14 can be distributed along all or part of the circumference of conduit body 12 in an orderly, or a random, fashion. In the non-limiting embodiment shown in FIG. 2, barbs 14 are provided such that there are two consecutive barbs along the circumference. Conduit body 12 can include more than one ring of barbs 14 along the same portion, spaced axially at a suitable distance along the conduit body 12. Utilizing a plurality of rings of barbs 14 at one end may provide enhanced gripping to the vessel. The barbs of one of the rings need not have the same dimensions as the barbs of another ring. The barbs need not be oriented and aligned along a ring as shown, and any arrangement may be substituted for that shown.

Preferred configurations of barbs 14 can be measured in terms of maximum load and maximum extension at maximum load with an axial tensile test. One such test includes affixing one end of a flexible vascular conduit having a 6 mm (0.24 inch) outer diameter for anchoring into the vessel. A general tensile rate of 12.7 cm/minute (5 inches/minute) is applied to one of the ends while measuring the tensile load and extension from the position from start of test to position at maximum load. The maximum tensile load measured in the range of about 1.1 to about 5.1 N (2.4±1.6 N) and the extension at maximum tensile load measured in the range of 13.8 mm to about 42.7 mm (27.2±12.7 mm).

Those skilled in the art are well aware of suitable means for fabricating structures, such as barbs 14, having a desired size and shape from substrate structures, such as a cylindrical body or ring of biocompatible material, or alternatively, for incorporating barbs into a cylindrical body. Preferably, the barbs are made of a rigid material. One particularly favored method of fabrication is laser cutting. Other methods such as chemical etching or micro-machining may also be used. Nano-fabrication may also be an acceptable way of forming small barbs. Other barbs have been fabricated by building out layers of silicon to form barbs in the range of 100 microns high by 80 microns wide, which structures resemble slanted pyramids.

Barbs 14 can be made of the same material as conduit body 12, or be a different material. As discussed previously, the material can be stainless steel or nitinol among others. When incorporating barbs to conduit body 12, it may be desirable that the material of the barbs be the same as the material of the conduit body. The barb tips can be cut, and then attached to the conduit body through known means of welding, soldering, or the like.

Graft covering 15 is preferably in intimate contact with conduit body 12. The graft covering 15 can have a delivery configuration when the body is in the radially compressed configuration, and a deployed configuration when the body is in the radially expanded configuration. Graft covering 15 can be a liner that extends entirely along the luminal wall 17 of conduit body 12. The graft covering can be made of material to inhibit fluid or blood located within the vascular conduit lumen 16 from passing through the graft covering. In other words, fluid flow is urged by the graft covering to enter into one end and exit out of the end of the vascular conduit. To better seal the ends of conduit body 12, a portion of graft covering 15 can be applied at the end. In one example, at least one of a proximal end 51 and a distal end 49 of graft covering 15 can extend from luminal wall 17 and radially outward around ends 21, 23 of conduit body 12, such that graft covering 15 has a portion folded around at least one of the ends of the body. Each of the ends 51, 49 may then extend longitudinally along exterior surface 18 of conduit body 12.

Preferably, ends 51, 49 extend to the respective gaps 30, 32 where it then can be attached to itself. As a result, the longitudinal distance of each of the first and second gaps 30, 32 should be long enough to allow plenty of the graft covering to attach to itself for a secure attachment. In this aspect, the exterior surface of intermediate portion 24 is left with bare material (i.e., without graft covering along the exterior surface) facing the vessel wall. This arrangement is found to stimulate neointimal or endothelial cell growth along this portion which can be beneficial for healing the vascular defect. Further, the graft covering along the interior surface along the intermediate portion can inhibit the degree of cell growth into the lumen of the vascular conduit for inhibiting thrombosis of the vascular conduit. Graft covering 15, as well as the conduit body, along the intermediate portion can also include a therapeutic agent described below to inhibit thrombosis and to accelerate cell growth and healing. The graft covering can attach to itself with a sufficient amount of the combination of pressure and heat for such purpose. Optionally, the graft covering can also be sutured to one another or may even be sutured to the conduit body. In another example, the graft covering can be applied to the tubular body with electrospinning.

Graft covering 15 can be formed from conventional materials well known in the medical arts. It is preferred that the graft covering have a porosity for sufficient capillarization and be relatively thin as possible (e.g., about 0.0005 inches to about 0.010 inches, and preferably about 0.001 to about 0.0035 inches). Examples of pore density and pore size for the graft covering, as well as other types of materials for a graft covering can be found in U.S. Pat. No. 7,244,444 to Bates, which is incorporated herein by reference in its entirety. A particularly preferred material is expanded polytetrafluoroethylene (ePTFE). Other materials that may be suitable in a particular case include, among others, polytetrafluoroethylene, silicone, polyurethane, polyamide (nylon), as well as other flexible biocompatible materials. Graft covering 15 can also be formed from known fabric graft materials such as woven polyester (e.g. DACRON®), or from a bioremodelable material. One exemplary graft material is THORALON® from Thoratec Corporation, Pleasanton, Calif., that can prevent leakage of fluid through the pores of the graft. THORALON® is a polyetherurethane urea blended with a siloxane containing surface modifying additive, and has been demonstrated to provide effective sealing of textile grafts. Another example is polyethylene, and in particular, an ultra-high molecular weight polyethylene (UHMwPE), commercially available as DYNEEMA®.

The graft covering may also include a bioremodelable material that can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931 to Cook et al., incorporated herein by reference.

FIG. 5 illustrates another embodiment of a vascular conduit 75, which is identical to vascular conduit 10 except for the following features. Vascular conduit 75 includes a second graft covering 76 along the exterior of the intermediate portion 24 of vascular conduit 75. Second graft covering 76 is adapted to facilitate rapid healing of a vascular defect or injury. In one aspect, second graft covering 76 may be further configured to dissolve into or disintegrate with the body after a period of time of healing, leaving the vascular conduit being configured like the one shown in FIG. 2. Second graft covering 76 may be attached to vascular conduit 75 by a biocompatible adhesive or suturing, and can be oriented such that barbs extend through the second graft covering. In some examples, second graft covering 76 can be a material capable of remodeling or promoting cell growth and/or promoting regrowth and healing of damaged or diseased tissue structures. The remodelable material can be ECM, SIS, remodelable or collagenous foam, foamed ECM, lyophilized SIS, vacuum pressed SIS, or the like.

The vascular conduits described herein can also include a coating of one or more therapeutic agents along a portion of the conduit body and/or the graft coverings. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose.

Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

Figure 5A:
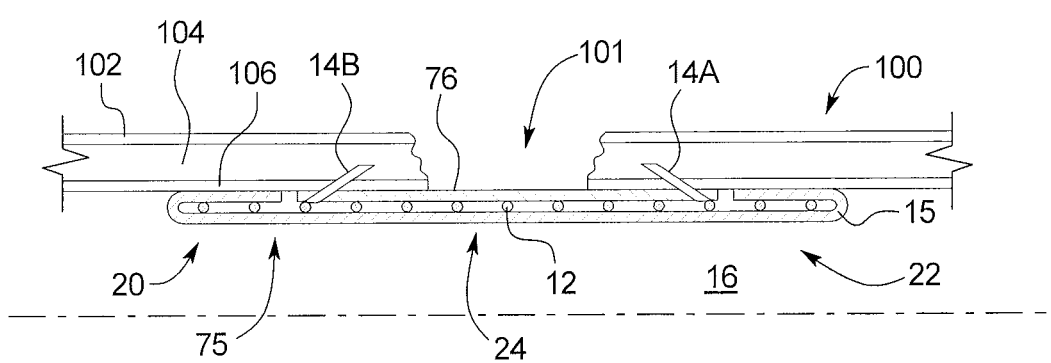
FIG. 5A is a partial elevation cross-sectional view depicting a deployed vascular conduit according to one of the described embodiments, engaged with a body vessel.

FIG. 5A illustrates vascular conduit 75 engaging with the body vessel 100 with a laceration 101 through the wall of the vessel. The components in this figure are exaggerated in order to better illustrate the implantation. Conduit 75 includes the first and second series of barbs 14A, 14B, with the barbs shown penetrating the tunica intima 106 and into the tunica media 104, and avoiding penetration of the tunica adventitia 102. Graft covering 15 is shown extending along the luminal wall of the conduit and everted around the ends of the conduit to extend to the respective gaps. As shown, the proximal and distal portions 20, 22 of conduit body 12 with graft covering 15 along the exterior surface can sealably engage with the vessel wall of body vessel 100 to prevent any leakage of blood for gaining hemostasis and to force blood to flow within lumen 16 of the vascular conduit for enhancing blood perfusion. Also shown is the intermediate portion of vascular conduit 10 with covering 76 sealing the edges of laceration 101.

FIG. 6A illustrates another embodiment of a conduit body 80. While additional description may be provided below with respect to FIG. 6A, it is understood that the descriptions also apply to the conduit bodies 12, 120 disclosed in FIGS. 3A and 7A. The conduit body 80 may be a stent structure 80, which is shown in FIG. 6A in a laid out view to show the entire structure 80 of the stent 80. As one of ordinary skill in the art understands, the stent structure 80 shown in FIG. 6A may be wrapped into a cylinder to form a cylindrical stent 80, where the top and bottom sides of the stent structure 80 in FIG. 6A are preferably integrally connected to each other. Further, one of ordinary skill in the art will recognize that the stent structure 80 shown in FIG. 6A is shown in its small diameter, collapsed configuration, which the stent 80 would be compressed to in order to minimally deliver the stent 80 to the desired treatment site. As shown, in this configuration, the struts 86, 88 are compressed so that they are generally parallel to each other and adjacent to the nearest struts 86, 88, 90. However, in the collapsed configuration, there may be a small angular orientation between adjacent struts 86, 88, 90. In the larger diameter, expanded configuration, the hoop struts 86 and the flex struts 88 expand away from each other so that the hoop cells 82 and flex cells 84 form zig-zag rings, with the hoop and flex struts 86, 88 becoming angularly oriented with respect to each other. Thus, whereas adjacent hoop struts 86 and adjacent flex struts 88 are oriented generally parallel to each other in the collapsed configuration, each of the adjacent hoop struts 86 and adjacent flex struts 88 are oriented with acute angles between them in the expanded configuration. However, the longitudinal struts 90 remain generally in the same orientation in both the collapsed and expanded configurations, which as shown in FIG. 6A is parallel to the axis of the stent 80. Although the stent structure 80 may be made from a ductile material so that the stent 80 is balloon-expandable, it may be preferable to make the stent structure 80 from an elastic material so that the stent 80 is self-expanding. The stent structure 80 may be sized as desired for particular applications, but the described stent structure may be particularly suited for a self-expanding stent with an expanded diameter of about 6 to about 10 mm.

As shown in FIG. 6A, the stent structure 80 has alternating hoop cells 82 and flex cells 84. The hoop cells 82 have a series of hoop struts 86 connected to each other through a series of hoop bends 92. The hoop cells 82 also have longitudinal struts 90 that extend substantially through the entire length of the hoop cells 82. The longitudinal struts 90 connect the hoop cells 82 and flex cells 84 together so that half of the longitudinal struts 90 connect to the proximally adjacent flex cell 84 and the other half of the longitudinal struts 90 connect to the distally adjacent flex cell 84. Thus, each longitudinal strut 90 is connected at one end to the outside of an adjacent flex cell bend 94, which connects two flex struts 88 together, and is connected at the other end to the inside of a hoop cell bend 92, which connects two hoop struts 86 together. Preferably, each hoop cell 82 has twenty-four hoop struts 86 and eight longitudinal struts 90. Thus, preferably, there are three hoop struts 86 between adjacent longitudinal struts 90 extending in opposite directions.

The flex cells 84 have a series of flex struts 88 connected to each other through a series of bends 94. Because the longitudinal struts 90 do not extend substantially through the length of the flex cells 84, the flex cells 84 only have flex struts 88 within each flex cell 84. As shown in FIG. 6B, the flex struts 88 may be generally parallel to each other in the collapsed configuration. Preferably, each flex cell 84 has twenty-four flex struts 88. Thus, it is particularly preferable for each of the hoop cells 82 to have the same number of hoop struts 86 as there are flex struts 88 in the flex cells 84. It is also preferable for the overall length of the flex cells 84 to be substantially the same as the overall length of the hoop cells 82. For example, overall length of the flex cells 84 and the hoop cells 82 is measured from the outside of opposite bends 92, 94 may be about 2.2 mm to about 2.5 mm. However, it is possible that the overall length of the flex cells 84 may be slightly longer than the overall length of the hoop cells 82, since the extra width of the flex struts 88 may also be applied to the flex cell bends 94. Despite slight differences such as this, the overall lengths of the flex cells 84 and hoop cells 82 are considered to be substantially equal to each other.

Because the flex cells 84 do not have longitudinal struts extending therethrough, the width of the flex struts 88 may be wider than the width of the hoop struts 86. For example, the width of the flex struts 88 may be about 0.165 mm, and the width of the hoop struts 86 may be about 0.112 mm. Thus, the width of the flex struts 88 is greater than the width of the hoop struts 86 by about 47% (i.e., 0.165/0.112−1). The widths of the flex and hoop struts 88, 86 are preferably generally uniform along the length of each strut 88, 86. The flex and hoop struts 88, 86 are also preferably entirely straight from end to end. The width of the longitudinal struts 90 is also preferably generally uniform along the length of each strut 90. The longitudinal struts 90 are also preferably entirely straight from end to end. The width of the longitudinal struts 90 may be substantially equal to the width of the hoop struts 86. The stent structure 80 is preferably cut from a cannula having a uniform thickness with a laser. For example, the thickness of the cannula may be about 0.197 mm after electropolishing so that the hoop struts 86, flex struts 88 and longitudinal struts 90 all have the same thickness of about 0.197 mm.

Like the conduit body 12 of FIG. 3A, the conduit body 80 of FIG. 6A has a proximal portion 20, an intermediate portion 24, and a distal portion 22. Although various lengths may be used for the conduit bodies, an overall length of about 45 mm to about 75 mm may be desirable for treating the superficial femoral artery. In order to position the barbs 14 in an area that is likely to engage undamaged tissue, the proximal and distal portions 20, 22 of the stent structure 80 have been shortened in the embodiment of FIG. 6A (and also FIG. 7A). As a result, the intermediate portion 24 has been lengthened. For example, a distance of about 30 mm to about 35 mm between the tips 43 of opposing barbs 14 may be desirable.

The end cells 96 preferably have longitudinal struts 90 that extend through the end cells 96 and extend away from the ends of the stent 80 to connect each end cell 96 to an interior second end cell 98. Preferably, there may be twenty-four struts in the end cells 96 and four longitudinal struts 90. The end cells 96 struts and longitudinal struts 90 connected to the end cells 96 may have a width that is wider than the width of the struts 86 in the hoop cells 82 but narrower than the struts in the second end cells 98, barbed cells 110, and flex cells 84. For example, the width of the struts in the end cells 96, including the longitudinal struts 90 connected thereto, may be about 0.135 mm, whereas the width of the struts 86 in the hoop cells 82 may be about 0.112 mm and the struts in the second end cells 96, barbed cells 110, and flex cells 84 may be about 0.165 mm.

The second end cells 98 preferably do not have any longitudinal struts 90 extending through the second end cells 98, and the second end cells 98 may have 24 struts. A series of longitudinal struts 112 extends across the gaps 30, 32 to connect the second end cells 98 to the barbed cells 110. The longitudinal struts 112 preferably do not extend through the second end cells 98 or the barbed cells 110, and thus, may be relatively short. For example, the gaps 30, 32 between adjacent bends of the second end cells 98 and the barbed cells 110 may be about 0.5 mm to about 1.5 mm, or about 1 mm, and thus, the longitudinal struts 112 need be no longer than necessary to span these gaps 30, 32.

The barbed cells 110 preferably have a similar structure as the second end cells 98 with the same strut width and no longitudinal struts 90 extending therethrough and having twenty-four struts. However, the struts in the barbed cells 110 may be slightly longer than the struts in the second end cells 98. For example, the struts in the barbed cells 110 may be about 2.8 mm to about 3.2 mm, or about 3.0 mm measured from the outer surface of the bends adjacent the second end cells 98 and the outer tips 43 of the barbs 14. Longitudinal struts 90 attached to the outer surface of the bends in the barbed cells 110 extend through adjacent hoop cells 82 to connect the barbed cells 110 to the hoop cells 82. Preferably, four longitudinal struts 90 connect the barbed cells 110 to the hoop cells 82. As illustrated, the barbs 14 are formed as an integral part of the struts in the barbed cells 110. Specifically, the barbs 14 are integral with the bends that connect adjacent struts in the barbed cells 110. Since the longitudinal struts 90 that connect the barbed cells 110 to the first hoop cell 82 in the intermediate portion 24 extend in the same direction as the barbs 14, barbs 14 cannot be placed on the bends where the longitudinal struts 90 are connected to the barbed cells 110. Thus, in the preferred embodiment, two barbs 14 are located between adjacent pairs of longitudinal struts 90. Therefore, preferably there may be eight barbs 14 on each barbed cell 110 directed toward the intermediate portion 24. As described above, the intermediate portion 24 is made up of alternating hoop cells 82 and flex cells 84.

FIG. 7A illustrates another embodiment of a conduit body 120 that is similar to the conduit bodies 12, 80 of FIGS. 3A and 6A. Unlike the stent 80 in FIG. 6A, the stent 120 in FIG. 7A has flex struts 122 that are the same width as the hoop struts 86. For example, the flex struts 122 in the flex cells 124 and the hoop struts 86 in the hoop cells 82 may be about 0.112 mm wide. However like FIG. 6A, the struts in the end cells 96 are preferably wider, for example, 0.135 mm. The struts in the second end cells 98 and the barbed cells 110 are also preferably wider, for example, 0.165 mm. As shown, adjacent flex struts 122 may also be angled toward each other in the collapsed configuration, whereas adjacent struts in the hoop cells 82, barbed cells 110, second end cells 98 and end cells 96 are generally parallel to each other. As a result, the end cells 96, second end cells 98 and barbed cells 110 provide higher radial force near the ends of the stent 120, and the flex struts 122 provide increased flexibility along the intermediate portion 24 of the stent 120.

FIG. 8A illustrates one embodiment of the barbs 14'. The barbs 14' may be formed by deflecting the struts 126 in the barbed cells 110 that are attached to the barbs 14' radially outward from the outer circumference 130 of the stent structure 12, 80, 120. Since the struts 128 in the barbed cells 110 that are connected to the hoop cells 82 with longitudinal struts 90 do not have barbs 14', these struts 128 are not deflected outward and remain within the outer circumference 130 defined by the stent structure 12, 80, 120. As shown in FIG. 8A, the barbs 14' and struts 126 attached thereto are deflected outward along substantially the entire length of the struts 126. That is, the struts 126 are deflected outward from the bends 132 opposite of the barbs 14' to the barb tips 43. As described above, the barbs 14' may also include flattened surfaces 66 that are generally parallel to the axis of the stent structure 12, 80, 120 and/or the outer circumference 130 of the stent 12, 80, 120, when the barbs 14' are in their outward deflected configuration. The barbs 14' may extend outward from the outer circumference 130 of the stent 12, 80, 120 so that the penetration depth 60 is about 0.25 mm to about 0.75 mm, or about 0.5 mm. For example, this may be measured from the outer surface of the adjacent struts 128 connected to the hoop cells 82 and the outer flattened surfaces 66 of the barbs 14'.

Preferably, the barbs 14' are formed by outwardly deflecting the struts 126 connected to the barbs 14', and then heat setting the struts 126 in the deflected state. For example, where the stent structure 12, 80, 120 is made from nitinol, the stent structure 12, 80, 120 may be expanded with a mandrel to its expanded configuration and the struts 126 attached to the barbs 14' may be deflected outward from the mandrel. The stent structure 12, 80, 120 may then be heated so that the stent structure 12, 80, 120 retains this expanded and deflected configuration as the unstressed state of the stent 12, 80, 120. If desired, the barbs 14' may be ground after deflecting and heat setting the barbs 14' and struts 126 to form the flattened outer surfaces 66. The stent structure 12, 80, 120 may then be elastically compressed to a smaller diameter to achieve a lower profile for delivery through a body vessel 1, 100. It may also be preferable for delivery to elastically compress the barbs 14' and struts 126 connected thereto inwardly so that the barbs 14' and struts 126 are aligned within the smaller diameter of the stent 12, 80, 120 and not extending outwardly therefrom. Accordingly, when the stent 12, 80, 120 is released at a treatment site, the stent structure 12, 80, 120 will self-expand to the unstressed expanded configuration and the barbs 14' and struts 126 will expand to the outwardly deflected configuration.

FIG. 8B illustrates another embodiment of the barbs 14". In contrast to the barb 14' shown in FIG. 8A, the barb 14" shown in FIG. 8B is not deflected outward along the entire length of the struts 128. Instead, a non-deflected portion 134 of each strut 128 in the barbed cells 110 remains within the outer circumference 130 of the stent structure 12, 80, 120. Thus, the barbs 14" are formed by the flexing only a portion 136 of the struts 128 in the barbed cells 110 radially outward. Preferably, the initiation of the deflected portion 136 may start at about 25% to about 50% of the length of the struts 128 from the bends 132 opposite of the barbs 14". In addition, it is preferable for the barbs 14" to be deflected along a radius 138 of about 0.5 mm to about 1.5 mm. Like the barbs 14' of FIG. 8A, it is preferable for the penetration depth 60 to be about 0.25 mm to about 0.75 mm, or about 0.5 mm.

As described above, a graft may be applied to the conduit body to prevent blood flowing through the lumen 16 of the conduit body from passing through the wall of the conduit body. The graft may be made of conventional materials and applied to the conduit body using conventional techniques. However, in one preferred embodiment, porous polyurethane or Thoralon may be used on the luminal surface of the conduit body and a non-porous polyurethane or Thoralon may be used on the abluminal surface. For example, the graft may be applied to the conduit body by dipping a mandrel into a mixture of polyurethane or Thoralon and a salt. Removal of the salt additive causes the resulting layer of polyurethane or Thoralon applied to the mandrel to be porous. If desired, a solvent may also be added to the mixture to adjust the viscosity of the mixture, and with subsequent layers, the solvent causes mixing and binding of the layers. Preferably, the salt is not removed (and the pores formed) until all of the graft layers are formed so that the solvents and mixing that results between the layers do not close the pores. After the inner layer is formed on the mandrel, the conduit body may then be primed with parylene and mounted onto the porous polyurethane or Thoralon layer on the mandrel. Because of the outward radial deflection of the barbs 14, it is generally unpreferred to apply an outer graft layer to the conduit body by dip coating, since the graft material may accumulate in the space between the deflected barbs 14 and the outer circumference 130 of the conduit body. Therefore, it is preferred to apply an outer graft layer with a nozzle from a syringe pump or an air pressure needle pump that is translated along the conduit body while the mandrel and conduit body are rotated. As a result, a thread of graft material is helically applied to the abluminal surface of the conduit body. Preferably, non-porous polyurethane or Thoralon is used for the outer graft layer. A solvent may also be mixed with the polyurethane or Thoralon to adjust the viscosity of the polyurethane or Thoralon so that the polyurethane or Thoralon flows through the nozzle, and the applied thread of material flows into adjacent sections of thread so that a contiguous outer layer is formed. Preferably, the graft has an overall thickness generally thicker than conventional graft layers to provide additional structural support for the treatment of lacerated vessels as described above. For example, the overall thickness of the graft may be about 0.15 mm to about 0.8 mm, or about 0.39 mm. The porous inner graft layer preferably provides the majority of the thickness of the overall graft, and the non-porous outer graft layer preferably provides the minority of the thickness of the overall graft. For example, the inner graft layer may be about 0.10 mm to about 0.7 mm thick, and the outer graft layer may be about 0.07 mm to about 0.2 mm thick.

FIGS. 9A-9B illustrate another embodiment of a conduit body 140. Like the conduit body 120 of FIG. 7A, the conduit body 140 has alternating hoop cells 82 and flex cells 124 throughout the majority of the intermediate portion 24. The hoop and flex cells 82, 124 may be substantially like the hoop and flex cells 82, 124 described above. In addition, the proximal and distal portions 20, 22 may each have a first end cell 96 that is substantially like the end cells 96 described above. However, unlike the embodiments described above, the barbed cells 142 may be the second end cells 142 located adjacent the first end cells 96. Structurally, the barbed cells 142 may be similar to the barbed cells 110 described above and may have the same strut width and may have barbs 14 deflected outward like FIGS. 8A and 8B. Preferably, the width of the struts 126, 146 in the barbed cells 142 is wider than the width of the struts in the first end cell 96 and the struts 86, 122 in the hoop and flex cells 82, 124 (i.e., a majority of the struts in the intermediate cells). However, the width of the struts 126, 146 in the barbed cells 142 is preferably substantially equal to the width of the struts in the first intermediate cell 144. The barbed cells 142 are each connected to a first intermediate cell 144 in the intermediate portion 24 with longitudinal struts 112 like the longitudinal struts 112 described above. The longitudinal struts 112 may be connected to non-barbed struts 146 in the barbed cells 142 in a similar manner that struts 128 are connected to the longitudinal struts 112 above, except that the longitudinal struts 112 in FIGS. 9A-9B are connected to the struts 146 at the same end that the struts 126 are connected to the barbs 14. The first intermediate cells 144 may be substantially like the second end cells 98 described above and may have the same width.

In a conduit body 140 designed to expand to about 5 mm to about 7 mm, or nominally about 6 mm, the length 148 of the first end cells 96, first intermediate cells 144, hoop cells 82 and flex cells 124 may be about 1.9 mm to about 2.5 mm, or more preferably about 2.2 mm. In a conduit body 140 designed to expand to about 7 mm to about 9 mm, or nominally about 8 mm, the length 148 of the first end cells 96, first intermediate cells 144, hoop cells 82 and flex cells 124 may be about 2.0 mm to about 2.6 mm, or more preferably about 2.3 mm. In a conduit body 140 designed to expand to about 9 mm to about 11 mm, or nominally about 10 mm, the length 148 of the first end cells 96, first intermediate cells 144, hoop cells 82 and flex cells 124 may be about 2.5 mm to about 3.1 mm, or more preferably about 2.8 mm. The length of the cells is preferably measured from the outer surface of opposing bends as shown in FIG. 9B. The length 150 of the barbed cells 142 is preferably longer than the length 148 of the first end cells 96, first intermediate cells 144, hoop cells 82 and flex cells 124 as measured from the outer surface of the bend 132 adjacent the first end cell 96 and a corresponding opposing imaginary bend 152 defined at the connection of the longitudinal struts 112 or the barbs 14. For example, for a conduit body 140 designed to expand to about 5 mm to about 9 mm, or nominally about 6 mm or about 8 mm, the length 150 of the barbed cells 142 may be about 2.2 to about 2.8, or more preferably about 2.5 mm. In a conduit body 140 designed to expand to about 9 mm to about 11 mm, or nominally about 10 mm, the length 150 of the barbed cells 142 may be about 2.8 to about 3.4, or more preferably about 3.1 mm. Preferably, the length 150 of the barbed cells 142 is about 5% to about 15% longer than lengths 148 of the first end cells 96, first intermediate cells 144, hoop cells 82 and flex cells 124. With reference to FIG. 8B, the non-deflected portion 134 of the struts 126 for a conduit body 140 designed to expand to about 5 mm to about 9 mm, or nominally about 6 mm or about 8 mm, is preferably about 0.5 mm to about 1.1 mm, or more preferably about 0.8 mm. The non-deflected portion 134 of the struts 126 for a conduit body 140 designed to expand to about 9 mm to about 11 mm, or nominally about 10 mm, is preferably about 1 mm to about 1.8 mm, or more preferably about 1.4 mm. Preferably, the non-deflected portion 134 extends about 15% to about 50% along the entire length of the struts 126 as measured from the bends 132 to the barb tips 43. The length 154 of the barbs from the imaginary bends 152 is preferably about 0.3 mm to about 0.8 mm, or more preferably about 0.55 mm. The length 156 of the longitudinal struts 112 connecting the barbed cells 142 and the first intermediate cells 144 measured from imaginary bend 152 to imaginary bend 152 is preferably about 0.55 to about 1.05 mm, or more preferably about 0.8 mm. The length 158 of the space between the barb tips 43 and the adjacent bends in the first intermediate cells 144 is preferably about 0.1 mm to about 0.6 mm, or more preferably about 0.3 mm. The length 154 of the barbs may overlap with between 28.6% and 88.9% of the length 156 of the longitudinal struts 112.

An advantage of the conduit body 140 of FIGS. 9A-9B is that the barbed cells 142 are located closer to the ends of the conduit body 140. This is helpful because the conduit body 140 may be used in emergency settings to reconnect fully transected vessels. In this procedure, the ends of the conduit body 140 may be inserted into opposing transected ends of a vessel to stop hemorrhaging and regain blood flow through the vessel. This type of procedure will typically be an open surgical procedure, where the conduit body 140 is placed directly into the wound site and the ends of the conduit body 140 are inserted directly into the separated ends of the transected vessel. In this type of procedure, it is desirable to minimize the portion of the conduit body 140 that must be inserted into the transected vessel ends. Thus, it would be preferred to locate the barbs 14 close to the ends of the conduit body 140, since the barbs 14 are intended to engage the inner wall of the transected vessel to secure the conduit body 140 to the vessel. Although it is desirable to have the barbed cells 142 as close as possible to the ends of the conduit body 140, it is preferred to have a first end cell 96 at the very ends of the conduit body 140 before the barbed cells 142, since the first end cells 96 expand the vessel lumen of each transected end and provide the barbed cells 142 with smoothly expanded vessel sections to secure the barbs 14 against.

The conduit body 140 of FIGS. 9A-9B is also advantageous because the barbs 14 are located within the gaps 30, 32 created by the longitudinal struts 112 connecting the barbed cells 142 and the first intermediate cells 144. As described above, the longitudinal struts 112 connecting the barbed cells 142 and the first intermediate cells 144 create a gap 30, 32 between the barbed cells 142 and the intermediate cells 144, since the longitudinal struts 112 do not extend through the barbed cells 142 or the first intermediate cells 144 like the longitudinal struts 90 of the hoop cells 82. The gaps 30, 32 between the barbed cells 142 and the first intermediate cell 144 may be larger than all other gaps in the conduit body 140 between adjacent cells. However, because the barb tips 43 are located within this larger gap 30, 32, the extra space is efficiently used and a compact barb arrangement is provided.

FIGS. 10-13 illustrate embodiments of a vascular conduit with an outer graft layer 164 that only partially covers the conduit body 162, 174 and is adhered to the inner layer 160. Although the inner graft layer 160 may be made of various materials and may be applied by various methods, the inner layer 160 is preferably made of an inner porous layer and an outer non-porous layer. For example, the inner porous layer, which forms the luminal surface of the vascular conduit, may be applied to a mandrel by dip coating the mandrel in a mixture of polyurethane or Thoralon, a solvent, and a salt. A solvent is preferably used with the polyurethane or Thoralon in applying each of the layers to maintain the desired viscosity and to cause mixing between each of the layers to bond the layers together. The porous layer is preferably formed by removing the salt from the first inner layer by dissolving the salt in a bath. However, this process is preferably done after all of the graft layers are formed and cured so that the solvents used in forming and bonding the layers do not cause the pores to close. After the inner porous layer has cured, the mandrel may be dip coated a second time in a mixture of polyurethane or Thoralon and a solvent to apply a non-porous layer around the outside of the porous layer. As noted, a solvent in the non-porous layer causes the polyurethane or Thoralon of the two layers to mix together so that the two layers bond together after the non-porous layer has cured.

After the non-porous layer has cured, the conduit body 162, 174 (which may be primed with parylene) is mounted onto the mandrel in an expanded state. An outer layer 164 may then be applied onto the outer surface of the conduit body 162, 174. The outer layer 164 is preferably made of a material that bonds to the inner layer 160 through the open spaces in the wall of the conduit body 162, 174. For example, a mixture that is substantially the same as the inner non-porous layer of polyurethane or Thoralon and a solvent may be used for the outer layer 164, or other suitable polymers and compatible solvents may be used. As a result, the solvent causes the inner non-porous layer 160 and the outer layer 164 to mix together through the openings in the conduit wall 162, 174. Thus, after curing, the two layers 160, 164 will be bonded together. Instead of dip coating as may be done for the inner layer 160, the outer layer 164 is preferably applied through a nozzle that directs a narrow stream of polyurethane or Thoralon and a solvent mixture onto the outer surface of the conduit body 162, 174 and the inner layer 160. The nozzle may then be translated as the mandrel and conduit body 162, 174 are rotated to apply a helical thread of graft material onto the conduit body 162, 174. As noted above, this prevents graft material from accumulating in the space underneath the deflected barbs 14. The mixture may be supplied to the nozzle by an air pressure needle pump or a syringe pump. Preferably, the nozzle opening is between about 33 gauge to about 18 gauge. The overall thickness of the graft layers 160, 164, including the porous first inner layer 160, non-porous second inner layer 160, and outer layer 164 is preferably about 0.15 mm to about 0.8 mm, or about 0.39 mm. The porous first inner layer is preferably thicker than the non-porous second layer and thicker than the outer layer 164. For example, the porous first inner layer may be about 0.10 mm to about 0.7 mm thick, and the non-porous second inner layer and outer layer 164 may each be about 0.07 mm to about 0.2 mm thick. It is also possible for the outer layer 164 to adhere to an inner layer 160 that is different from the outer layer 164 but compatible for bonding the two layers 160, 164 together. For example, polyethylene terephthalate (PET) or Dacron fabric may be used for the inner layer 160, and a polyurethane or Thoralon and a solvent mixture may be applied as the outer layer 164. Thus, in this case, the polyurethane and polyethylene terephthalate bond to each other because they are compatible with each other even though the inner and outer layers 160, 164 are not the same material.

As shown in FIGS. 10-11, one or more of the end cells may be completely coated 166 by the outer layer 164. This may be done by translating the nozzle along a short pitch so that adjacent windings of the outer layer 164 flow together to form a contiguous outer layer 166. The contiguous outer layer 166 at each end may cover part of the barbed cells 110, but preferably the contiguous ends 166 do not substantially cover the barb tips 43. Although the conduit body 162 shown in FIGS. 10-11 is comparable to the conduit body 120 of FIG. 7A, the graft layers 160, 164 may be applied to any type of conduit body as desired. For example, it may be desirable to apply the graft layers 160, 164 of FIGS. 10-11 to the conduit body 140 of FIG. 9A. However, when applied to FIG. 9A, the contiguous outer layer 166 at the ends would preferably be shorter and only cover the first end cell 96 and part of the barbed cell 142. Preferably, the middle portion 168 is only partially coated by the outer layer 164. For example, in FIG. 10, a bead 170 of the outer layer 164 is applied to each of the longitudinal struts 90 to encapsulate a small portion of the conduit body 162 and secure the outer layer 164 and inner layer 160 together. The rest of the middle portion 168 may remain uncovered by the outer layer 164, which leaves the conduit body 162 less constrained to permit improved flexibility along the middle portion 168.

In FIG. 11 the outer layer 164 may be applied as a helical thread 172 along the middle portion 168 with a pitch large enough so that adjacent windings 172 do not contact each other. Thus, the space between the windings 172 is uncovered by the outer layer 164, and the inner layer 160 is only bonded to the outer layer 164 along the path of the helical thread 172. Preferably, the pitch of the outer layer 172 along the middle portion 168 is about half the length of each cell to about 1½ times the length of each cell. That is, each cell may have two full windings 172 of the outer layer 164 or less, but preferably at least two thirds of a winding 172 per cell. More preferably, each cell has at least one full winding 172 of the outer layer 164. Thus, more preferably, the pitch of the helical outer layer 172 is about 0.5 to about 1 times the length of each cell. One advantage of this embodiment, is that the outer layer 164 may be applied as a continuous process from the proximal end to the distal end. For example, the nozzle can begin translating at one end along a short pitch that forms a contiguous outer layer 166. At the beginning of the middle section 168, the nozzle can continue dispensing the thread of graft material, but the pitch can be increased so that adjacent windings 172 no longer contact each other. Then, when the nozzle reaches the opposite end of the middle section 168, the pitch can be shortened again to form the other contiguous end 166.

As shown in FIGS. 12-13, the inner and outer graft layers 160, 164 may also be applied to conventional conduit bodies 174 without barbs 14. For example, the graft layers 160, 164 may be applied to a stent 174 with radiopaque eyelets 175 and alternating hoop cells 82 and flex cells 124. For ease of illustration, the stents 174 of FIGS. 12-13 are shown in an as-cut configuration in a fully laid-out view. However, it is understood that the graft layers 160, 164 are preferably applied in the expanded state as described above. As shown in FIG. 12, one or more end cells may have a contiguous outer layer 166, while the middle portion 168 may have a helical outer layer 172 that does not contact adjacent windings 172. As shown, the helical outer layer 172 preferably has a pitch of about the length of each cell. The pitch of the helical outer layer 172 may also be about 0.5 to about 1.5 times the length of each cell, and more preferably, about 0.5 to about 1 times the length of each cell.

As shown in FIG. 13, only a small portion at the ends of the end cells is contiguously coated 166. It is desirable for at least a small portion at the ends to be contiguously coated 166 to ensure that the inner layer 160 forms a clear opening at the ends without any portion of the inner layer 160 forming a flap at the ends. However, once the inner layer 160 is secured to the ends by at least an outer layer 166 lip of graft material, or using some other method of securement, it may be desirable for substantially the entire length of the stent 174 to be only partially covered by the outer layer 164. In FIG. 13, it may also be desirable for the helical outer layer 172 to have a shorter pitch 172A along the hoop cells 82 and a longer pitch 172B along the flex cells 124. This may provide greater securement along the hoop cells 82 and greater flexibility along the flex cells 124. For example, the pitch 172A along the hoop cells 82 may be about 0.2 to about 0.7 times the length of each hoop cell 82, and the pitch 172B along the flex cells 124 may be about 0.6 to about 1 times the length of each flex cell 124.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

We claim:

1. A perfusion device for repair of a body vessel, comprising:
   a tubular body being radially self-expanding from a compressed configuration to an expanded configuration, the tubular body having a proximal end and a distal end and defining a lumen about a longitudinal axis, the tubular body comprising a proximal portion, a distal portion, and an intermediate portion, the proximal and distal portions each comprising at least two end cells each comprising a single series of struts and bends interconnected to the struts, and the intermediate portion comprising at least two or more intermediate cells each comprising a single series of struts and bends interconnected to the struts;
   wherein the at least two end cells comprise a first end cell and a second end cell, the first end cell of the proximal portion being located most-proximal in the proximal portion and the first end cell of the distal portion being located most-distal in the distal portion, and the second end cell in each of the proximal portion and the distal portion being located adjacent the respective first end cell toward the intermediate cells, each of the second end cells comprising integral barbs directed toward the intermediate cells, the barbs being located at the bends interconnecting the struts, and the struts connected to the barbs being deflected radially outward from an outer circumference of the tubular body;
   wherein the at least two or more intermediate cells comprise a first intermediate cell located at each end of the intermediate portion, each of the first intermediate cells being located adjacent a respective one of the second end cells;
   wherein each of the second end cells is connected to a respective adjacent first intermediate cell with a longitudinal strut, the longitudinal strut not extending through the second end cells or the intermediate cells, a gap being defined by a length of the longitudinal strut between each of the second end cells and each of the first intermediate cells, the gap between each second end cell and each first intermediate cell being larger than another gap between adjacent cells in the tubular body, tips of the barbs being disposed within the gap between each second end cell and each first intermediate cell;
   a first graft attached to and extending along a length of a luminal side of at least one of the proximal portion and the distal portion, extending around at least one of the proximal end and the distal end of the tubular body, and extending along a length of an abluminal side of the at least one of the proximal portion and the distal portion; and
   a second graft attached to and extending continuously along a longitudinal length of the intermediate portion, wherein the barbs pierce the second graft, and wherein the second graft is comprised of a material adapted to dissolve more quickly than a material of the first graft.

2. The device of claim 1, wherein each of the struts connected to the barbs comprises a first portion located away from the barbs and a second portion located adjacent the barbs, the first portion, in the expanded configuration, not being deflected radially outward and being disposed within the outer circumference of the tubular body and the second portion being deflected radially outward, the first portion being 15% to 50% of an entire length of each strut.

3. The device of claim 1, wherein an outer surface of each of the barbs, extends 0.25 mm to 0.75 mm from the outer circumference of the tubular body in the expanded configuration.

4. The device of claim 3, wherein the outer surface of each of the barbs extends 0.5 mm from the outer circumference of the tubular body in the expanded configuration.

5. The device of claim 1, wherein each of the barbs in the expanded configuration is capable of penetrating into a tunica intima and a tunica media of said body vessel upon insertion of said device into said body vessel, and not into a tunica adventitia of said body vessel.

6. The device of claim 1, wherein each of the tips comprises a surface parallel with the longitudinal axis in the expanded configuration.

7. The device of claim 1, wherein each of the barbs has a delivery configuration when the tubular body is in the compressed configuration, the barbs and struts connected to the barbs being compressed within the outer circumference of the tubular body in the delivery configuration.

8. The device of claim 1, wherein the second end cells each comprise fewer struts than each of the first end cells.

9. The device of claim 1, wherein a width of the struts in the second end cells is wider than a width of a majority of the struts in the intermediate cells.

10. The device of claim 1, wherein a width of the struts in the second end cells being substantially equal to a width of the struts in the first intermediate cells.

11. The device of claim 1, wherein a width of the struts in the second end cells and a width of the struts in the first intermediate cells are each wider than a width of the struts in intermediate cells located between the first intermediate cells.

12. The device of claim 1, wherein the gap between each second end cell and each first intermediate cell being larger than all other gaps between adjacent cells in the tubular body.

13. The device of claim 1, wherein a length of the second end cells defined by opposing bends within the second end cells is 5% to 15% longer than lengths of all other cells within a tubular structure defined by opposing bends within each cell.

14. The device of claim 1, wherein the first graft comprises an inner layer extending along a luminal surface of the tubular body, an outer contiguous layer disposed at each end of the tubular body and extending along an abluminal surface of the tubular body, the outer contiguous layers being bonded to the inner layer between the first and second end cells and barb tips of the barbs being substantially uncovered by the outer contiguous layers, and wherein the second graft is disposed between the outer contiguous layers and extending along an abluminal surface of the tubular body, the second graft being bonded to the inner layer between a plurality of the intermediate cells, the second graft only partially covering the tubular body between the outer contiguous layers.

15. The device of claim 14, wherein the second graft is a helical thread with a pitch of 0.5 to 1 times a length of each intermediate cell, adjacent windings of the helical thread not contacting each other such that space between the windings is uncovered by the second graft.

16. The device of claim 1, wherein an outer surface of each of the barbs extends 0.25 mm to 0.75 mm from the outer circumference of the tubular body in the expanded configuration, each of the tips comprises a surface generally parallel with the longitudinal axis in the expanded configuration, a width of the struts in the second end cells is wider than a width of a majority of the struts in the intermediate cells, the gap between each second end cell and each first intermediate cell being larger than all other gaps between adjacent cells in the tubular body.

17. The device of claim 1, wherein each of the struts connected to the barbs comprises a first portion located away from the barbs and a second portion located adjacent the barbs, the first portion not being deflected radially outward and being disposed within the outer circumference of the tubular body and the second portion being deflected radially outward, the first portion being 15% to 50% of an entire length of each strut, each of the barbs is capable of penetrating into a tunica intima and a tunica media of said body vessel upon insertion of said device into said body vessel, and not into a tunica adventitia of said body vessel, a width of the struts in the second end cells being substantially equal to a width of the struts in the first intermediate cells, a length of the second end cells defined by opposing bends within the second end cells is longer than a length of the first end cells defined by opposing bends within the first end cells, and the length of the second end cells is 5% to 15% longer than lengths of all other cells within a tubular structure defined by opposing bends within each cell.

18. The device of claim 1, wherein a width of the struts in the second end cells is wider than a width of the struts in the first end cells, the width of the struts in the second end cells and a width of the struts in the first intermediate cells are each wider than a width of the struts in intermediate cells located between the first intermediate cells, and the gap between each second end cell and each first intermediate cell being larger than all other gaps between adjacent cells in the tubular body.

19. The device of claim 18, the width of the struts in the second end cells is substantially equal to the width of the struts in the first intermediate cells.

20. The device of claim 1, wherein the first graft comprises a porous material on the luminal side, and comprises a non-porous material on the abluminal side.

21. A perfusion device for repair of a body vessel, comprising:
  a tubular body being radially expandable from a compressed configuration to an expanded configuration, the tubular body having a proximal end and a distal end and defining a lumen about a longitudinal axis, the tubular body comprising a proximal portion, a distal portion, and an intermediate portion, the proximal and distal portions each comprising at least two end cells each comprising a single series of struts and bends interconnected to the struts, and the intermediate portion comprising at least two or more intermediate cells each comprising a single series of struts and bends interconnected to the struts;
  wherein the at least two end cells comprise a first end cell and a second end cell, the first end cell of the proximal portion being located most-proximal in the proximal portion and the first end cell of the distal portion being located most-distal in the distal portion, and the second end cell in each of the proximal portion and the distal portion being located adjacent the respective first end cell toward the intermediate cells, each of the second end cells comprising integral barbs directed toward the intermediate cells, the barbs being located at the bends interconnecting the struts, and the struts connected to the barbs being deflected radially outward from an outer circumference of the tubular body;
  wherein the at least two or more intermediate cells comprise a first intermediate cell located at each end of the intermediate portion, each of the first intermediate cells being located adjacent a respective one of the second end cells;
  wherein each of the second end cells is connected to a respective adjacent first intermediate cell with a longitudinal strut, the longitudinal strut not extending through the second end cells or the first intermediate cells, a gap being defined by a length of the longitudinal strut between each of the second end cells and each of the first intermediate cells, the gap between each second end cell and each first intermediate cell being larger than another gap between adjacent cells in the tubular body, tips of the barbs being disposed within the gap between each second end cell and each first intermediate cell, wherein each of the tips comprises a surface parallel with the longitudinal axis in the expanded configuration; and
  wherein a length measured along the longitudinal axis of the second end cells defined by opposing bends within the second end cells is longer than a length measured along the longitudinal axis of the first end cells defined by opposing bends within the first end cells.

22. The device of claim 21, wherein at least a portion of the barbs comprise a porous portion adapted to extend into bodily tissue.

\* \* \* \* \*